United States Patent [19]
Kishi

[11] Patent Number: 5,311,877
[45] Date of Patent: May 17, 1994

[54] WAKING DEGREE MAINTAINING APPARATUS

[75] Inventor: Atsuhide Kishi, Sagamihara, Japan

[73] Assignee: Mazda Motor Corporation, Hiroshima, Japan

[21] Appl. No.: 954,147

[22] Filed: Sep. 30, 1992

[30] Foreign Application Priority Data

Oct. 2, 1991 [JP] Japan .................. 3-255553

[51] Int. Cl.$^5$ ............ A61B 5/04; A61B 5/103; G08B 23/00
[52] U.S. Cl. .................. 128/732; 128/782; 340/575; 340/576
[58] Field of Search ........ 128/774, 782, 732, 739–742, 128/706, 905; 340/573, 575, 576; 186/272

[56] References Cited

U.S. PATENT DOCUMENTS

| | | | |
|---|---|---|---|
| 3,877,466 | 4/1975 | Montor | 128/732 |
| 3,924,606 | 12/1975 | Silva et al. | 128/732 |
| 4,220,142 | 9/1980 | Rosen et al. | 340/575 |
| 4,725,824 | 2/1988 | Yoshioka | 340/575 |
| 4,883,067 | 11/1989 | Knispel et al. | 128/732 |
| 4,928,090 | 5/1990 | Yoshimi et al. | 340/575 |
| 4,953,111 | 8/1990 | Yamamoto et al. | 340/575 |

FOREIGN PATENT DOCUMENTS

| | | | |
|---|---|---|---|
| 56-2227 | 1/1981 | Japan . | |
| 9113584 | 9/1991 | PCT Int'l Appl. | 128/639 |

Primary Examiner—Lee S. Cohen
Assistant Examiner—Marianne Parker

[57] ABSTRACT

A waking degree maintaining apparatus of this invention estimates a waking degree of a person on the basis of a correlation between brain waves and the reaction time or between the blinking frequency and the reaction time, and discriminates a drop in waking degree on the basis of the obtained waking degree. A stimulus according to the waking degree is presented to maintain the person in a waking state of a predetermined level. The waking degree of a person is recovered to a normal state, not only in a low waking degree state, but also in an over-stained state.

15 Claims, 38 Drawing Sheets

| SUBJECT \ VIBRATION | 0 % | | | 40 % | | | 80 % | | |
|---|---|---|---|---|---|---|---|---|---|
| TG | 0.89 | 1800 | 1500 | 0.95 | 480 | 1200 | 0.80 | 300 | 350 |
| OH | 0.83 | 1800 | 1800 | 0.97 | 1200 | 1500 | 0.83 | 1200 | 1500 |
| TM | 0.82 | 300 | 350 | 0.83 | 350 | 350 | 0.83 | 1800 | 1500 |
| IZ | 0.97 | 350 | 1200 | 0.94 | 600 | 1800 | 0.98 | 480 | 1800 |
| AR | 0.89 | 1200 | 1500 | 0.68 | 1500 | 900 | 0.74 | 1800 | 1800 |

FIG. 10

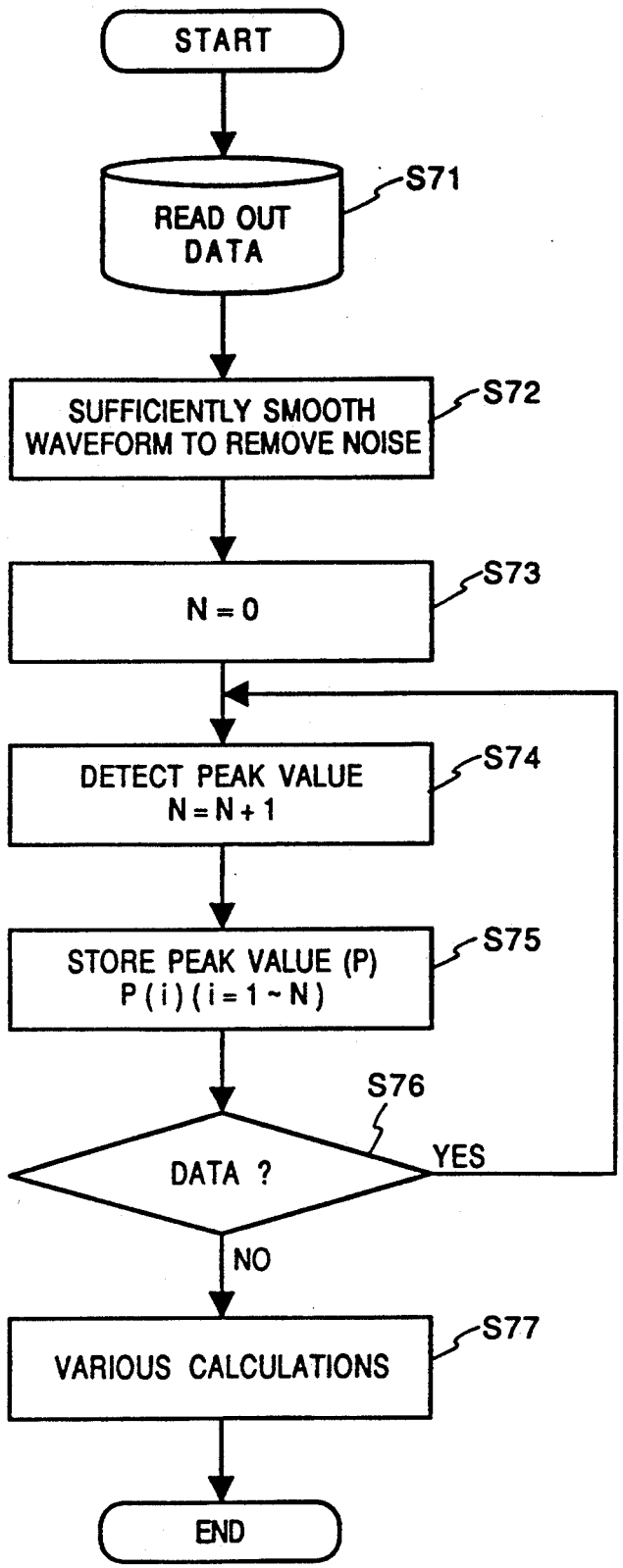
F I G. 28

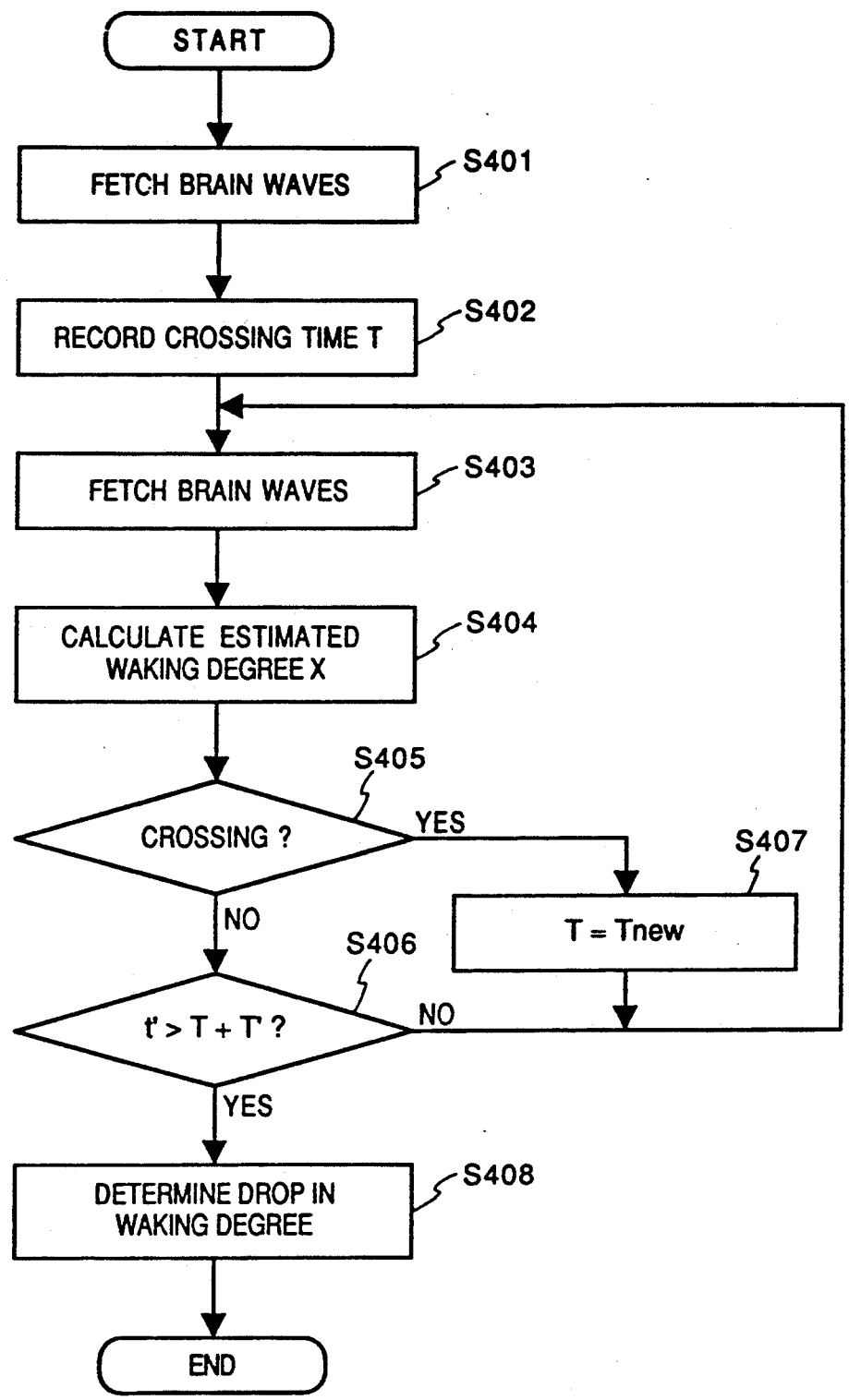
F I G. 33

WAKING DEGREE MAINTAINING APPARATUS

BACKGROUND OF THE INVENTION

1. Field of the Invention

The present invention relates to a waking degree maintaining apparatus for discriminating a drop in waking degree of a person, and presenting a stimulus according to the drop in waking degree, thereby maintaining the person in a waking state of a predetermined level.

2. Description of the Related Art

When a person performs monotonous work for a long period of time, he or she experiences a drop in waking degree (attentiveness), and recovers a waking state after a while. There is no method to quantitatively measure such a rhythm of the waking state in which normal and low waking levels repetitively appear, although it can be obscurely recognized.

It is known that the waking degree drops due to work or an operation of a vehicle for a long period of time, and the reaction time at that time is prolonged. However, no method for quantitatively measuring how much the reaction time is prolonged is available.

When a drop in waking degree of a person is estimated based on, e.g., the blinking frequency, a predetermined trigger value is set in eye movement data. When the data exceeds the trigger value, it is determined that an eye movement occurs, and the number of times of eye movements is counted. As the trigger value, an eye movement waveform for about 1 to 5 minutes is observed, and a value with which a stable blinking frequency can be measured is experimentally set.

In recent years, the necessity for quantitative determination of the waking state, i.e., a technique for quantitatively recognizing the time characteristics of a drop in waking degree, and preventing the drop in waking degree, has increased. However, a method for detecting and determining the drop in waking degree or the state of tension itself with high precision has not been found yet.

For example, in the measurement of the blinking frequency, the above-mentioned method is an effective method capable of obtaining a stable result when a base line fluctuation is small, and when the measurement time is short enough to be able to ignore the influence of a time in which electrodes for the measurement become adapted to a living body and are degraded. However, in a long-time measurement, since the base line fluctuates, the initially set trigger value often becomes ineffective, and the trigger value must be re-set.

When the time waveform of the eye movement is measured using, e.g., a computer, the waveform is differentiated, and time-series data of the differential values is similarly triggered to measure the blinking frequency. However, the same problem as described above is posed, or the influence of a disturbance such as an electrode vibration which often occurs upon measurement under vibration cannot be eliminated.

SUMMARY OF THE INVENTION

It is an object of the present invention to provide an apparatus, which can determine a drop in waking degree on the basis of an estimated waking degree, and can realize biological feedback control according to the determined waking degree.

The present invention comprises the following arrangement as means for achieving the above-mentioned object.

More specifically, the invention of claim 1 comprises means for calculating an estimated waking degree of a person, means for calculating an average peak value and a standard deviation of waking degree amplitudes of the calculated estimated waking degree, means for determining a drop in waking degree on the basis of the calculated average peak value and standard deviation, and means for, when the drop in waking degree is determined, presenting a predetermined stimulus.

The invention of claim 5 comprises means for calculating an estimated waking degree of a person, means for calculating a period of a waking degree rhythm and a standard deviation of the calculated estimated waking degree, means for determining a drop in waking degree on the basis of the calculated period and standard deviation, and means for, when the drop in waking degree is determined, presenting a predetermined stimulus.

Furthermore, the invention of claim 10 comprises means for calculating an estimated waking degree of a person, means for setting a stimulus amount according to the estimated waking degree, and means for presenting a stimulus corresponding to the set stimulus amount.

In the above arrangement, the apparatus of the present invention obtains an estimated waking degree with high precision, and presents a stimulus according to the obtained waking degree, thereby maintaining a person in an optimal waking state.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 1 to 17 are views for explaining a waking degree estimation method according to an embodiment of the present invention;

FIGS. 24 to 33 are views for explaining the rhythm characteristics of a waking degree;

DETAILED DESCRIPTION OF THE PREFERRED EMBODIMENT

The preferred embodiment of the present invention will be described below with reference to the accompanying drawings.

<Description of Waking Degree Estimation Method>

Figure 1:
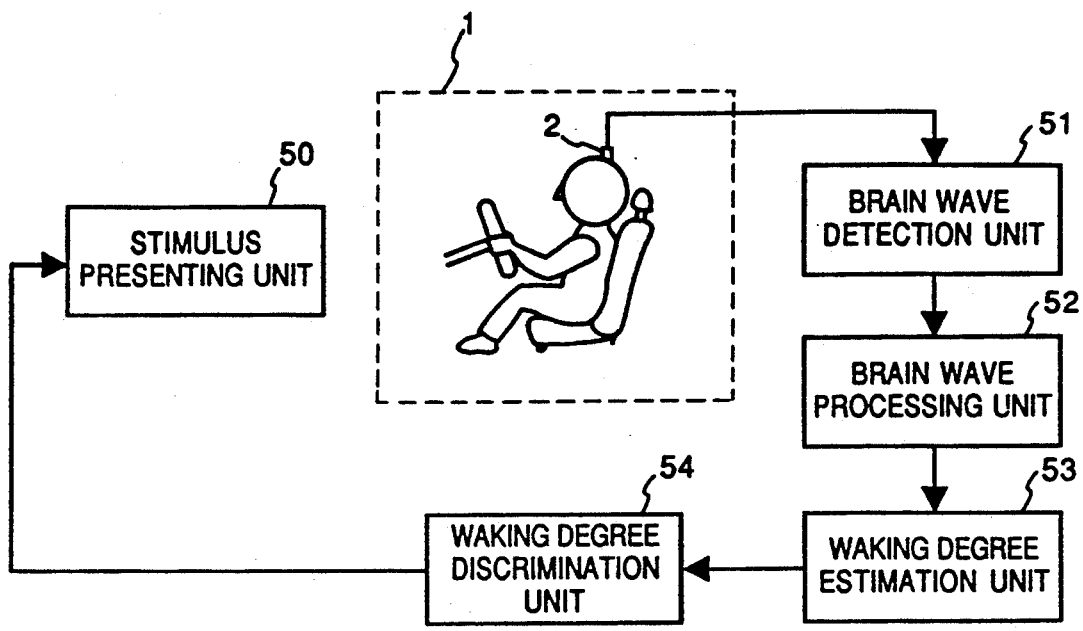

FIG. 1 is a block diagram showing the overall arrangement of a waking degree maintaining apparatus according to this embodiment. The waking degree maintaining apparatus shown in FIG. 1 absolutely quantifies the waking degree of a person, and presents a stimulus such as a vibration, tone, smell, or the like to, e.g., a driver (operator), thereby maintaining the driver in a waking state of a predetermined level in a biological feedback manner. Thus, the driver can be prevented from dozing off or becoming excessively excited.

In the waking degree maintaining apparatus shown in FIG. 1, a brain wave detection unit 51 detects brain waves from a driver 1 as a subject using an electrode 2 attached to his or her head, and amplifies the detected brain waves. A brain wave processing unit 52 performs signal processing of the brain wave signals from the brain wave detection unit 51, thereby converting the brain waves into physical amounts allowing easy waking degree estimation. More specifically, the brain wave processing unit 52 fetches the brain wave signal amplified by the brain wave detection unit 51 through an A/D converter (to be described later), and performs digital filtering processing of the fetched brain wave signal to separate it into frequency bands of a $\delta$ wave (1 to 3 Hz), a $\theta$ wave (3 to 6 Hz), an $\alpha$ wave (8 to 13 Hz), and a $\beta$ wave (13 to 30 Hz). In this manner, the unit 52 processes the input signal into physical amounts necessary for waking degree evaluation.

A waking degree estimation unit 53 calculates an estimated value closely associated with the waking state on the basis of waking degree estimation parameters (to be described later) and the brain wave band data. A waking degree discrimination unit 54 determines a stimulus amount to be presented on the basis of the waking degree estimated by the waking degree estimation unit 53. A stimulus presenting unit 50 presents a proper stimulus or stops it according to an instruction from the waking degree discrimination unit 54.

The waking degree maintaining apparatus of this embodiment estimates the waking degree of a driver on the basis of the brain waves and reaction time, and gives an optimal stimulus to the driver using the estimated information in a biological feedback manner.

The principle of biological feedback control adopted in this embodiment will be described below with reference to FIG. 2.

Figure 2:
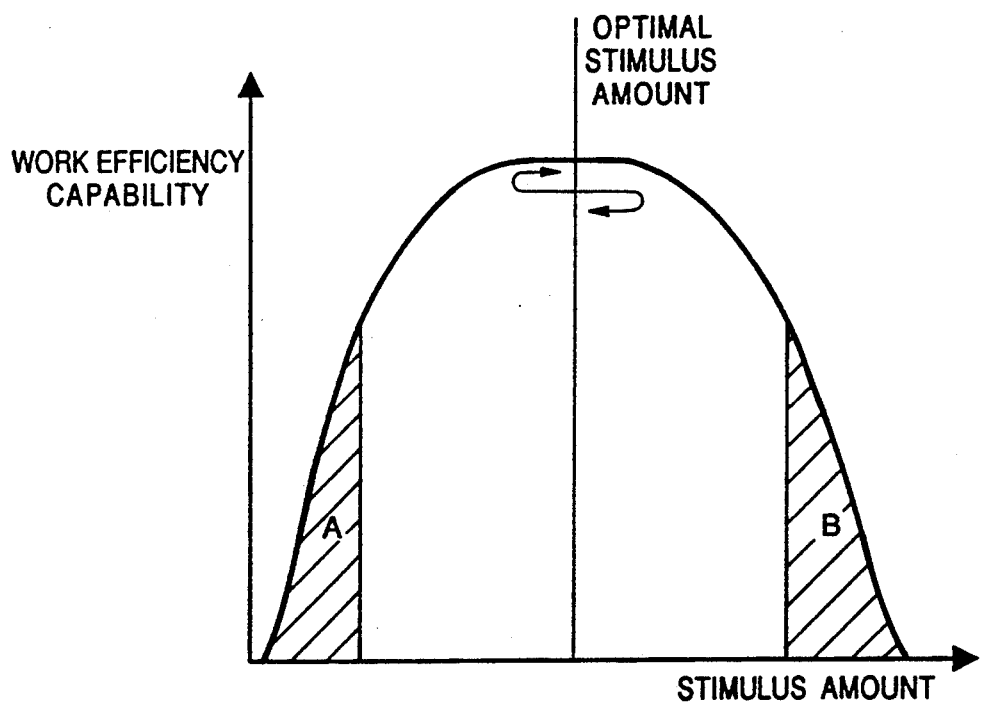

FIG. 2 is a graph which is popular in psychology or human engineering. In FIG. 2, the work efficiency or capability is plotted along the ordinate. If a description is limited to a driving state, the work efficiency or capability corresponds to a target steering operation or judgment. The stimulus amount is plotted along the abscissa, and a visual stimulus, an aural stimulus, a tactual stimulus, an olfactory stimulus, and the like may be proposed. These stimuli correspond to the scenery seen from the front window, noise, vibration, or smell in the passenger room in the driving state.

A hatching portion B in FIG. 2 represents a region where when the stimulus amount exceeds a predetermined level, a driver can no longer perform an adequate operation, and finally causes a panic (over-waking). For example, when a driver increases the vehicle speed in a high-speed traveling state, he or she can no longer follow a road environmental change, and becomes disabled to perform a steering operation, or when a vehicle spins, he or she cannot avoid it.

A hatching portion A in FIG. 2 represents a region where since the stimulus amount is too small to keep the driver attentive, the driver is bored, and his or her waking degree drops. For example, a drop in waking degree in a monotonous driving state on a freeway is known. In this connection, a conventional doze alarming apparatus aims at generating an alarm to a driver when this region is reached.

As can be understood from the above description, a person cannot respond to information or an environmental change exceeding a certain amount or level, and similarly experiences a drop in waking degree for a stimulus amount below a predetermined level. From this viewpoint, it is most desirable for a safety apparatus to clarify an optimal stimulus amount of each person, and to give an effective stimulus adjusted according to physiological conditions near the optimal stimulus amount although the stimulus amount varies individually. This situation is illustrated as the optimal stimulus amount at the central portion of FIG. 2.

In this embodiment, detection of the waking state of a person, and presentation of a stimulus according to the detected waking state allow to maintain the optimal waking state shown in FIG. 2 in principle.

A waking degree estimation parameter determining device for determining parameters upon calculation of the waking degree in the waking degree estimation unit 53 will be described first.

The waking degree estimation parameter determining device simultaneously measures the reaction time and brain waves which have a high correlation with the waking degree, and performs multiple regression analysis on the basis of the obtained brain wave data and reaction time data, thereby determining waking degree estimation parameters.

Figure 3:
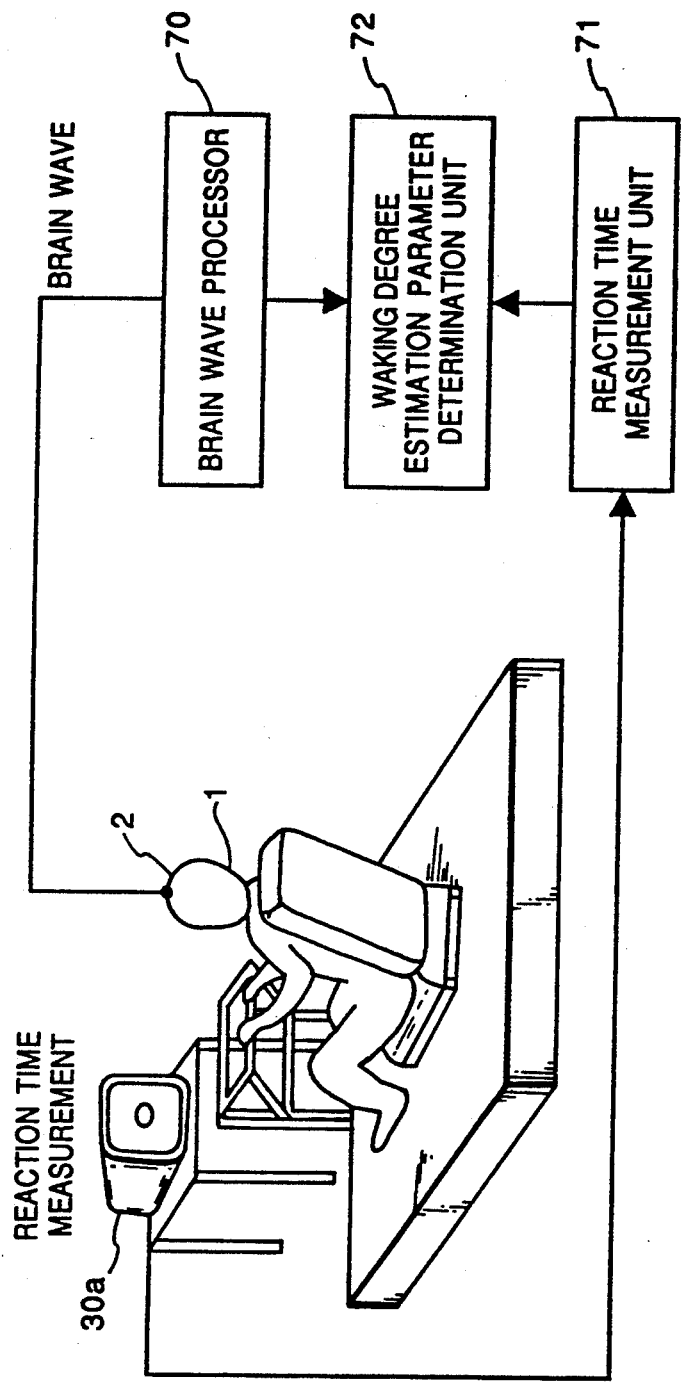

FIG. 3 is a schematic block diagram of the waking degree estimation parameter determining device. FIG. 3 illustrates a situation wherein this device measures the reaction time and brain waves of a person for a long period of time, and estimation parameters can be obtained by analyzing the obtained reaction time and brain waves.

In FIG. 3, a brain wave processor 70 measures brains waves from the electrode 2 attached to the subject 1, and a reaction time measurement unit 71 measures a reaction time of the subject 1 in response to a given stimulus. Based on these measurement results, a waking degree estimation parameter determination unit 72 estimates a waking degree inherent to the subject.

Figure 4:
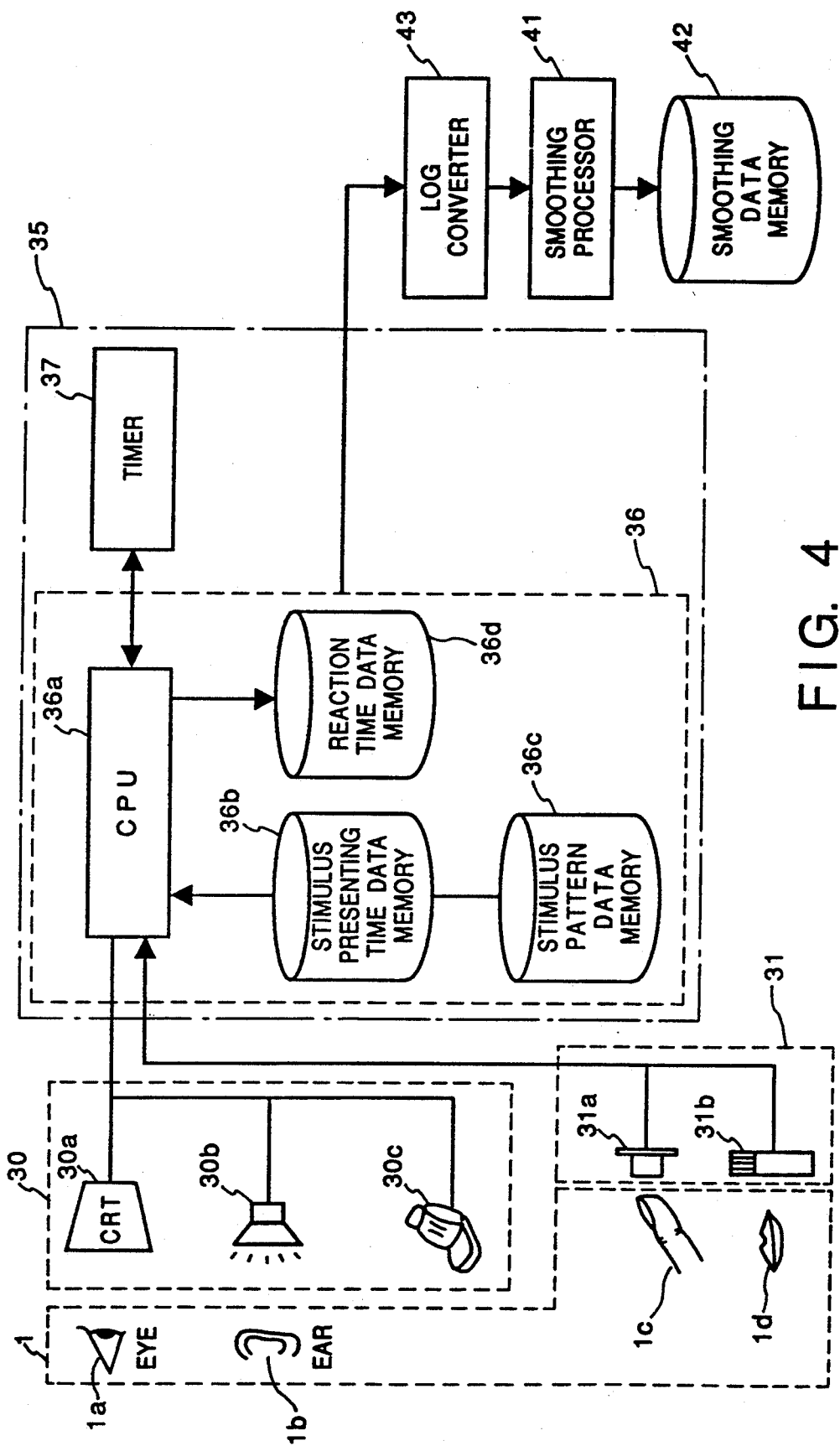

FIG. 4 is a block diagram showing an arrangement of the reaction time measurement unit 71 for measuring the reaction time (selective reaction time) of a person for a long period of time. In FIG. 4, a reaction stimulus presenting unit 30 generates stimuli for measuring reactions to the subject 1 under the control of a selective reaction time measurement unit 35, and the reactions from the subject 1 are input to the selective reaction time measurement unit 35 through a reaction input unit 31.

The selective reaction time measurement unit 35 is constituted by a main controller 36 including a CPU 36a for controlling the entire unit and memories for storing various data, and a timer 37 for setting a time for presenting a stimulus for obtaining a reaction, and measuring the reaction time. The data memories include a stimulus presenting time data memory 36b for storing data associated with a time to present a stimulus for obtaining a reaction, a stimulus pattern data memory 36c for storing a stimulus pattern for obtaining a reaction, and a reaction time data memory 36d for storing the measured reaction time. Note that these memories comprise disk devices or semiconductor memories as storage media.

The reaction stimulus presenting unit 30 is constituted by a CRT 30a for generating a stimulus as an image to the subject 1, a loudspeaker 30b for generating a stimulus tone, and a seat 30c, which incorporates a vibrator, and can generate a tactual stimulus for pressing a living body, and on which the subject can sit to allow an easy reaction to the stimulus.

The reaction input unit 31 has a button 31a with which the subject 1 reacts to the stimulus with his or her finger 1c, and a microphone 31b with which the subject 1 reacts to the stimulus with his or her voice. The reaction from the reaction input unit 31 is stored in the reaction time data memory 36d as reaction time data through the CPU 36a of the selective reaction time measurement unit 35.

Note that a LOG converter 43 LOG-converts the reaction time data fetched from the reaction time data memory 36d, and outputs the converted data to a smoothing processor 41. A smoothing data memory 42 stores a smoothing data outputted from the smoothing processor 41.

A reaction time measurement device and a measurement processing sequence according to this embodiment will be described below.

Figure 5:
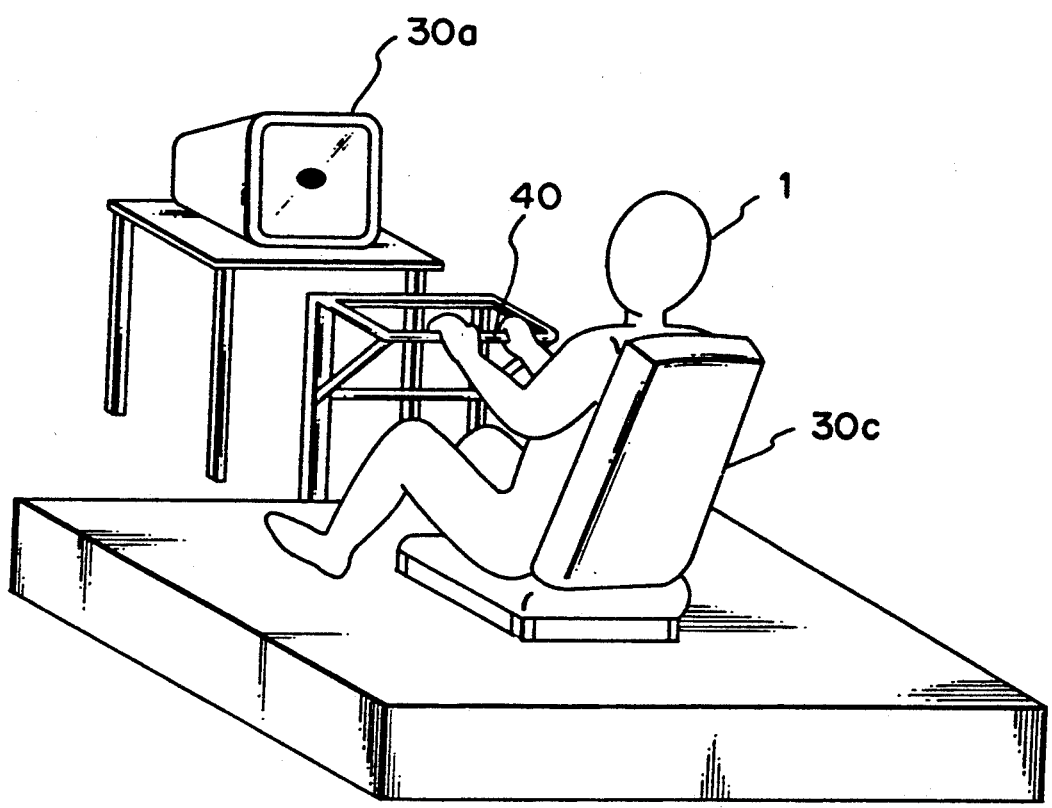

FIG. 5 shows a case wherein a CRT is used as the reaction stimulus presenting unit in a reaction time measurement situation in this embodiment. In FIG. 5, the subject 1 sits on the seat 30c, and holds a bar 40 with a plurality of reaction buttons (not shown). A stimulus for obtaining a reaction is displayed on the CRT 30a in front of the subject 1, and is set to instantaneously disappear. The subject 1 is instructed to select and depress a button as quickly as possible according to a predetermined rule when the stimulus is displayed on the screen of the CRT 30a.

The CRT 30a instantaneously displays a colored circular mark, which is large and bright enough to see, according to the stimulus presenting time and stimulus pattern data set in the selective reaction time measurement unit 35. There are three colors, and the presenting order of these colors is randomly set. The display time interval is also randomly set. Note that the number of colors is not limited to three.

Figure 6:
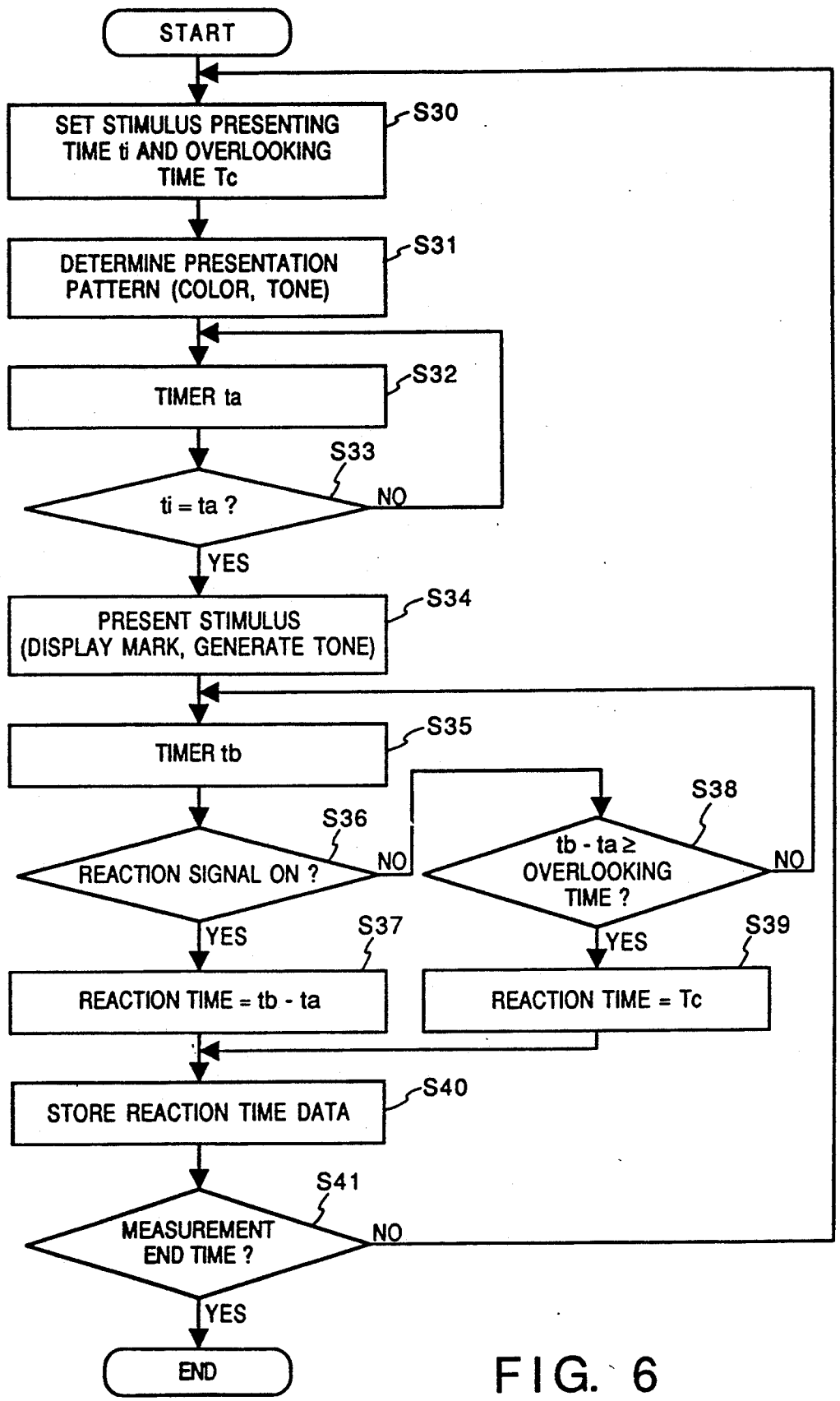

FIG. 6 is a flow chart showing a reaction time measurement sequence in this embodiment. In step S30 in FIG. 6, a stimulus presenting time $t_i$, a measurement end time, and an overlooking time $T_c$ when the waking degree drops, and a reaction is delayed are set. The stimulus presenting time $t_i$ is obtained by generating a random number, and the presenting time interval can be uniformly and randomly selected to fall within a range between 5 seconds and 30 seconds. In this case, the time interval and the distribution may be arbitrarily set. The measurement time is preferably set to fall within a range between 30 minutes and several hours.

In step S31, the stimulus presenting pattern for selecting colors as stimuli is randomly set. In this case, colored circular marks (red, blue, and yellow) are set. The randomness upon generation of stimuli may have certain tendency, and stimuli may be presented in a given order in an extreme situation. This depends on the degree of attentiveness, and when monotonous characteristics are to be emphasized, the stimuli may be presented in a pattern that can be easily expected.

In step S32, the timer 37 informs the current time $t_a$ to the CPU 36a. In step S33, it is checked if the stimulus presenting time $t_i$ set in step S30 coincides with the current time $t_a$. If YES in step S33, i.e., if the set stimulus presenting time is reached, the predetermined stimulus pattern is presented to the subject in step S34. In this manner, a wait time can be set until the stimulus is generated.

In step S35, the timer 37 informs the current time $t_b$ after stimulus presentation to the CPU 36a. In step S36, it is checked if a reaction signal from the subject 1 is detected. If YES in step S36, $t_b - t_a$ is calculated as the reaction time in step S37. However, if NO in step S36, the flow advances to step S38 to compare the pre-set overlooking time $T_c$ when the waking degree drops and a reaction is delayed with the wait time $t_b - t_a$. If it is determined in step S38 that the wait time does not exceed $T_c$, the flow returns to step S35 to input the current time $t_b$, and the reaction signal is waited again in step S36. However, if YES in step S38, i.e., if the wait time exceeds $T_c$, it is determined that the subject overlooked the presented stimulus, and the reaction time is set to be $T_c$ for subsequent processing in step S39.

In step S40, the obtained reaction time data with respect to the stimulus presenting time is stored in the reaction time data memory 36d. In step S41, the CPU 36a checks if the measurement end time is reached. If NO in step S41, the flow returns to step S30 to repeat the above-mentioned processing until the measurement end time is reached. However, if it is determined in step S41 that the measurement end time has been reached, this processing is ended.

Figure 7:
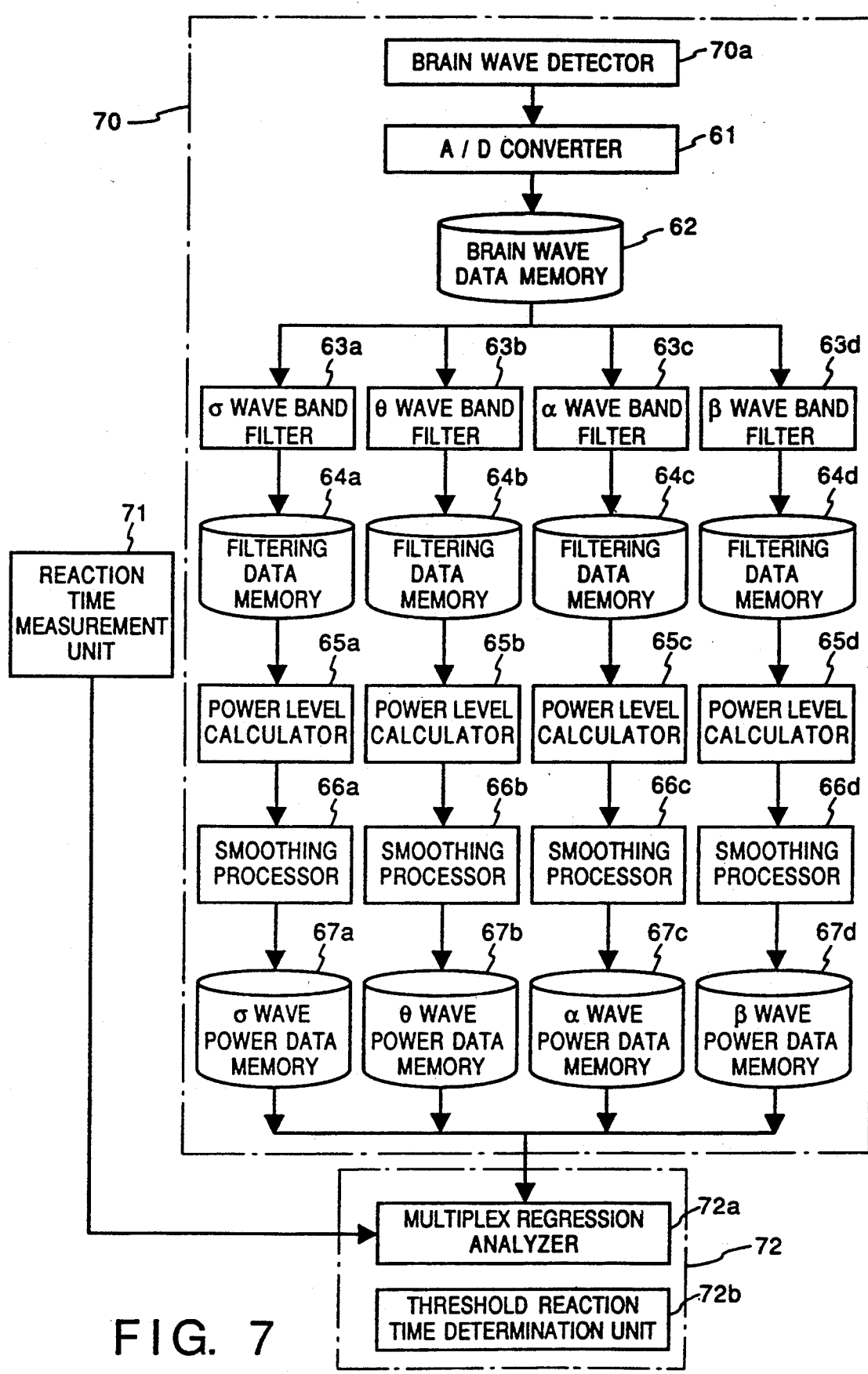

FIG. 7 is a block diagram showing the arrangement of the brain wave processor 70. In a brain wave detector 70a, a brain wave electrode (not shown) is attached to the head of a person using a special-purpose conductive adhesive, and brain waves obtained through the electrode are amplified by a head amplifier (not shown) to remote noise. Thereafter, the brain waves are amplified by a brain wave amplifier (not shown).

The brain wave signal from the brain wave detector 70a is stored as brain wave data in a brain wave data memory 62 through an A/D converter 61. This data is separated by digital filters (63a to 63d) into a $\delta$ wave band, a $\theta$ wave band, an $\alpha$ wave band, and a $\beta$ wave band, and the band data are stored in corresponding filtering data memories (64a to 64d). Then, each power level calculator (65a to 65d) calculates an average power level from brain wave data of the corresponding band. In this case, an averaging time $T_p$ (about 1 second) is properly determined. In order to convert the obtained average power data into an average power level having a high correlation with the waking degree, the average power data is smoothed by a corresponding smoothing processor (66a to 66d). A method of setting a smoothing time at that time will be described later. The average power data is stored in a power data memory (67a to 67d) of the corresponding band.

As for the smoothing processing of brain waves, in order to obtain a correspondence with the reaction time, a power level from the stimulus presenting time to a time before the smoothing time associated with the brain waves is averaged, and the average power level is determined as the brain wave power level at that time. This case, smoothing times ($T\delta$, $T\theta$, $T\alpha$, and $T\beta$) of the brain waves of the respective bands must be determined.

These parameters must be set to obtain the highest correlation between the smoothed brain waves (four variables) and the reaction time. For this reason, the reaction time is used as a target variable, and four variables, i.e., the $\delta$ wave power level, the $\theta$ wave power level, the $\alpha$ wave power level, and the $\beta$ wave power level are used as explanation variables. Then, multiple regression analysis is performed by a multiple regression analyzer 72a while changing the smoothing time of the brain waves. Of multiple correlation coefficients obtained for various combinations of smoothing parameters, the maximum multiple correlation coefficient is detected, and the combination of smoothing parameters at that time are determined as the optimal smoothing times for the brain waves. At the same time, parameters a1, a2, a3, and a4 obtained from the multiple regression analyzer, and a multiple regression formula using these parameters as a waking degree estimation formula are determined. Although a variable to be predicted in this case is the reaction time, it can be considered that the reaction time has a high correlation with the waking degree.

Figure 8:
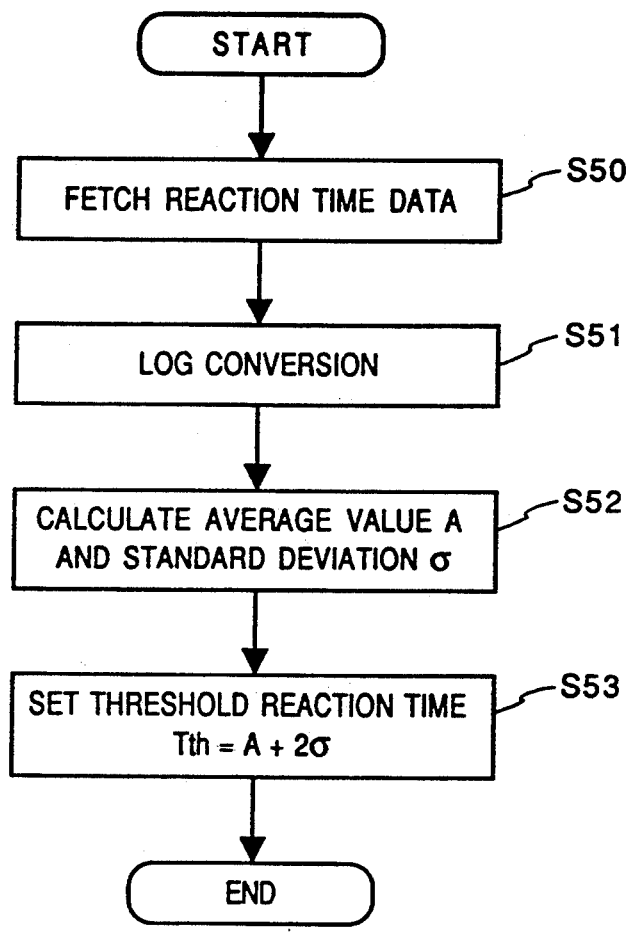

The waking degree can be quantitatively calculated. In this case, a threshold value at which stimulus presentation is started must be determined. FIG. 8 is a flow chart showing a determination sequence at that time.

In step S50 in FIG. 8, reaction time data is fetched. In step S51, the reaction time data is LOG-converted. In step S52, an average value A and a standard deviation are calculated. In general, it is known that the reaction time has a Gaussian distribution. In order to detect that the waking level is considerably shifted from an average value, a threshold reaction time Tth = A + $\sigma$ to A + 2$\sigma$ is set in step S53. When the reaction time becomes longer than this threshold reaction time, it can be determined that the wake degree is beginning to drop. Similarly, when the reaction time becomes shorter than a reaction time Tth = A − $\sigma$ to A −2$\sigma$, it can also be determined that the waking degree is considerably high. Based on this principle, Tth is used as a threshold waking degree at which an awakening stimulus begins to be given.

The obtained Tth, T$\delta$, T$\theta$, T$\alpha$, T$\beta$, a1, a2, a3, and a4, and a multiple regression formula using these parameters are determined as waking degree estimation parameters.

The constituting elements of the waking degree maintaining apparatus of this embodiment will be described in detail below.

<Brain Wave Detection Unit>

An electrode for detecting brain waves is attached to the head of a subject (in this case, a driver of a vehicle) using a special-purpose conductive adhesive, and the obtained brain waves are amplified by a head amplifier (not shown) to remove noise. Thereafter, the brain waves are amplified by a brain wave amplifier (not shown).

<Brain Wave Processing Unit>

Figure 9:
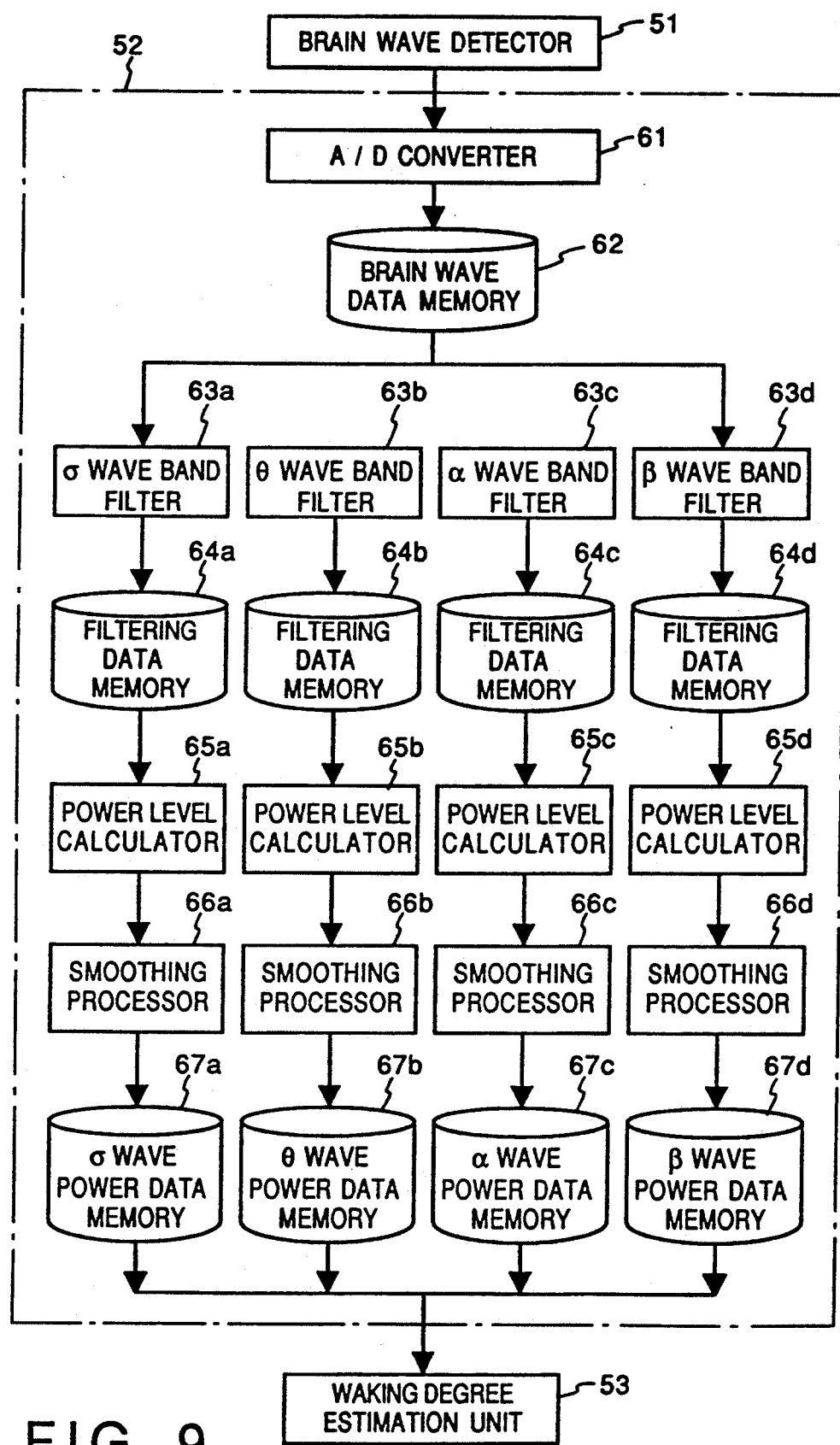

FIG. 9 is a block diagram of the brain wave processing unit 52. Since the brain wave processing unit shown in FIG. 9 has substantially the same function as that of the brain wave processor shown in FIG. 7, except for a brain wave power level calculation method, the same reference numerals in FIG. 9 denote the same parts as in FIG. 7, and a detailed description thereof will be omitted.

<Waking Degree Estimation Unit>

The waking degree estimation unit 53 calculates the waking degree based on the band power data of the brain waves processed by the brain wave processing unit 52 using the waking degree estimation parameters and the multiple regression formula obtained by a waking degree estimation parameter determination device shown in FIG. 3. The unit 53 supplies the calculated value to the waking degree discrimination unit 54.

The waking degree is expressed by the following estimation formula:

$$Waking\ Degree = a1^*P\delta + a2^*P\theta + a3^*P\alpha + a4^*P\beta + a5 \quad (1)$$

where P$\delta$, P$\theta$, P$\alpha$, and P$\beta$ are the average powers of the $\delta$, $\theta$, $\alpha$, and $\beta$ wave bands.

Figure 11:
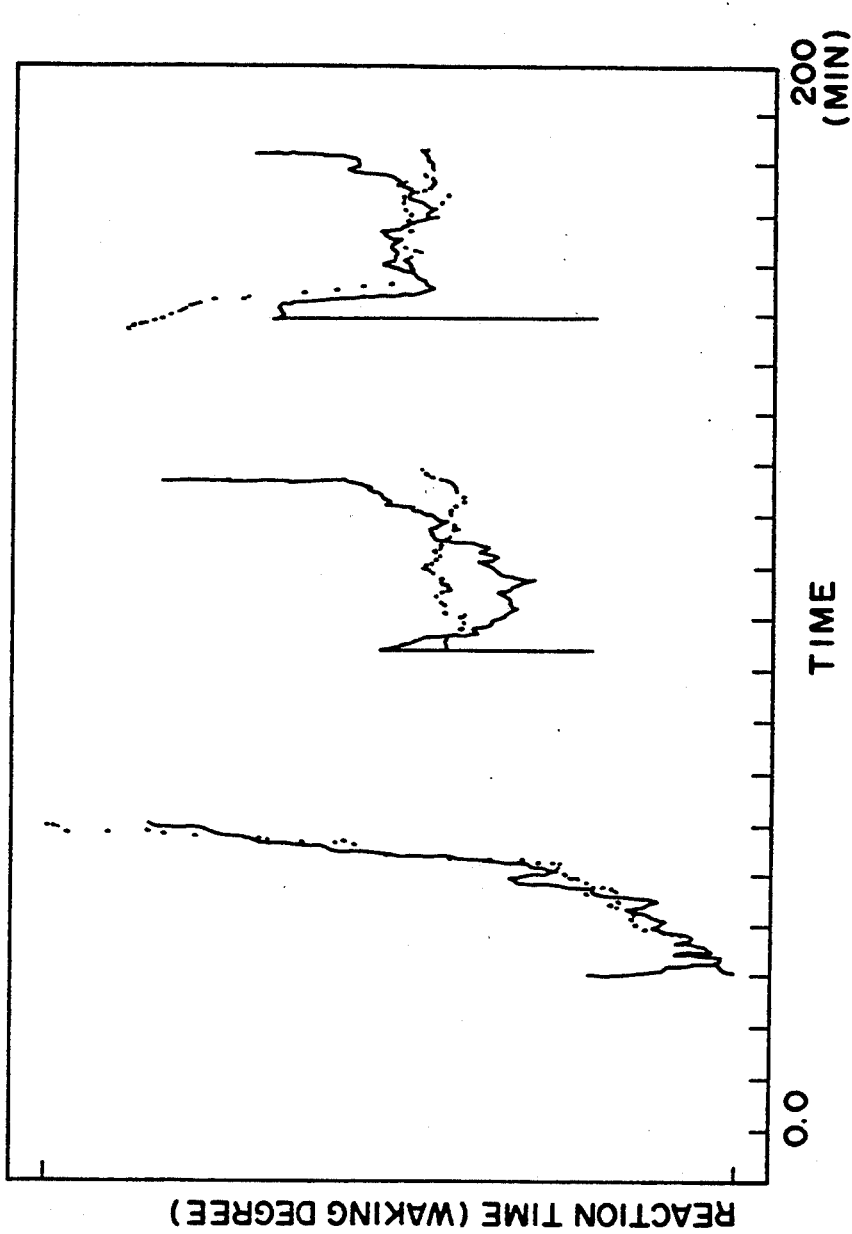

FIGS. 10 and 11 show waking degrees estimated by the above-mentioned method.

FIG. 10 shows maximum multiplex correlation coefficients, and the smoothing times of reaction times and brain waves of the respective subjects obtained under the corresponding vibration conditions of a vibration device. In FIG. 10, numerical values in each column respectively represent from the left the multiplex correlation coefficient, and the smoothing times (seconds) of the reaction time and the brain waves when the corresponding multiplex correlation coefficient is obtained. Note that the multiplex correlation coefficient is rounded at the third decimal place.

FIG. 11 shows the reaction time and a change in predicted value of the reaction time over time according to the multiplex regression formula based on the results shown in FIG. 10. In FIG. 11, the reaction time is plotted along the ordinate, and the elapsed time is plotted along the abscissa. In FIG. 11, dots represent the reaction times, and solid curves represent values estimated from brain waves. Note that a division between adjacent data represents a break.

In this example, the multiplex correlation coefficient between the reaction time and the brain waves is 0.89, and this means that the above-mentioned method is effective for estimating the waking degree, and the waking degree can be finely estimated. The multiplex correlation coefficient can assume a value ranging between 0.7 and 0.98 although it depends on each subject.

<Waking Degree Discrimination Unit>

The processing sequence in the waking degree discrimination unit 54 will be described below with reference to the flow chart shown in FIG. 12.

Figure 12:
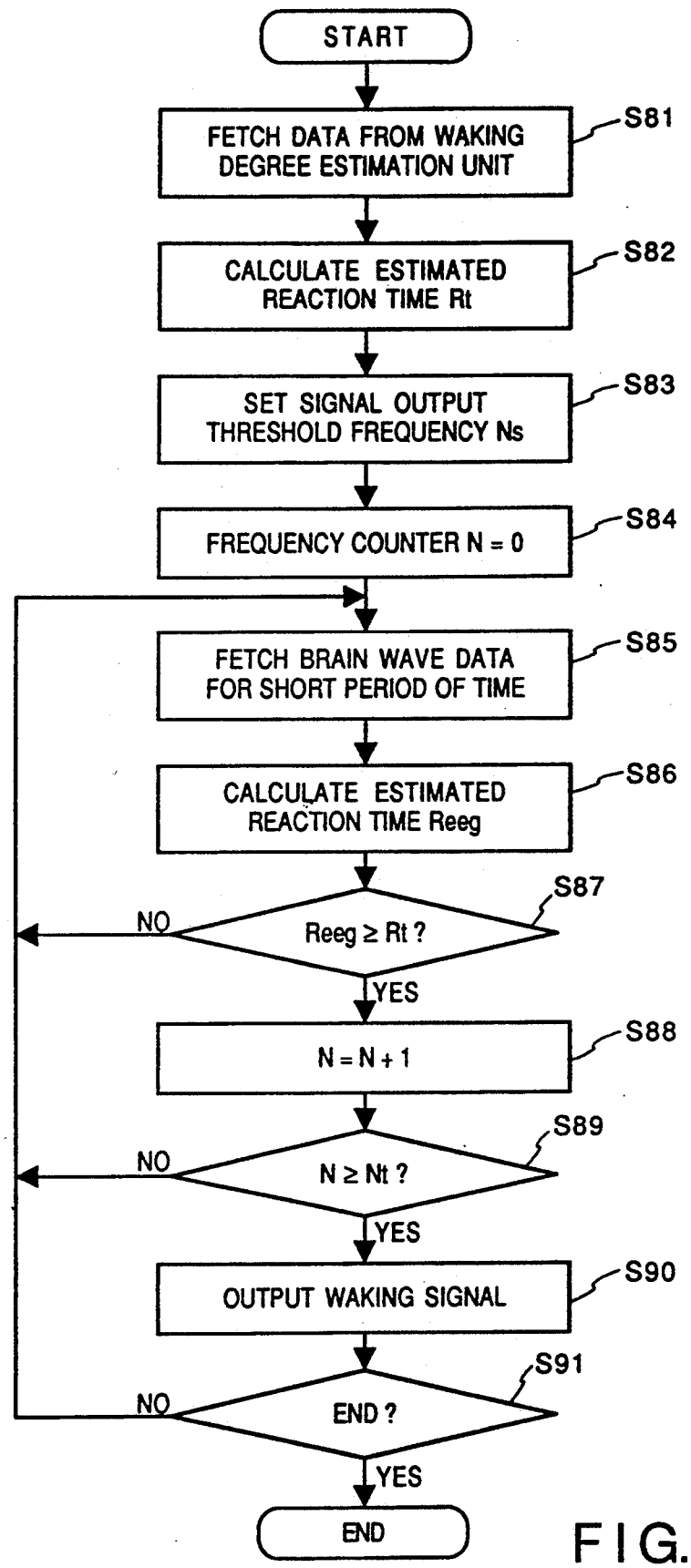

In step S81 in FIG. 12, the waking degree estimated by the waking degree estimation unit 53 is fetched. In step S82, a reaction time Rt corresponding to the waking degree is estimated. In this case, it is dangerous to immediately determine based on the fact that Rt exceeds Tth once that the waking state changes. This is because Rt may vary due to some cause.

Thus, a signal output threshold frequency Ns is set in step S83. In step S84, 0 is set in a frequency counter N representing the frequency that Rt exceeds Tth. More specifically, when Rt exceeds Tth at a frequency larger than the predetermined frequency Ns, it is determined that the waking degree has dropped. Note that the Rt sampling time can be appropriately determined. Rt determined in this manner is used as a reference upon discrimination of a drop in waking degree.

In step S83, Ns is determined, and the frequency counter value is set to be 0. Thereafter, in step S85, brain wave data for a short period of time is fetched. In step S86, an estimated reaction time Reeg (waking degree) is calculated using the estimation parameters and the multiple regression formula.

In step S87, Reeg and Rt are compared with each other. If the estimated reaction time Reeg does not exceed Rt, the flow returns to step S85, and processing for fetching brain wave data and calculating the estimated reaction time Reeg again is repeated. However, if it is determined in step S87 that the estimated reaction time Reeg exceeds Rt, the content of the frequency counter N is incremented by one in step S88. In step S89, the content of the frequency counter N is compared with the frequency Nt. If NO in step S89, the flow returns to step S85; otherwise, i.e., if it is determined that the content of the frequency counter N exceeds the frequency Nt, it is determined that the waking state is abnormal. In step S90, a waking down signal representing a drop in waking degree is output. The waking down signal is supplied to the stimulus presenting unit.

In step S91, it is checked if the processing is ended.

Note that a mechanism for, when Reeg does not exceed Rt for a while after it exceeds Rt, determining it as noise, and resetting the counter N may be arranged.

<Stimulus Presenting Unit>

Upon reception of the waking down signal from the waking degree discrimination unit 54, the stimulus presenting unit 50 outputs a stimulus having an awakening effect such as a tone, a vibration, a smell, or the like to the driver 1 of the vehicle for a predetermined period of time until a stop signal is input. In this case, the type of stimulus or its presentation method may be those obtained by an awakening stimulus setting device to be described below.

Figure 13:
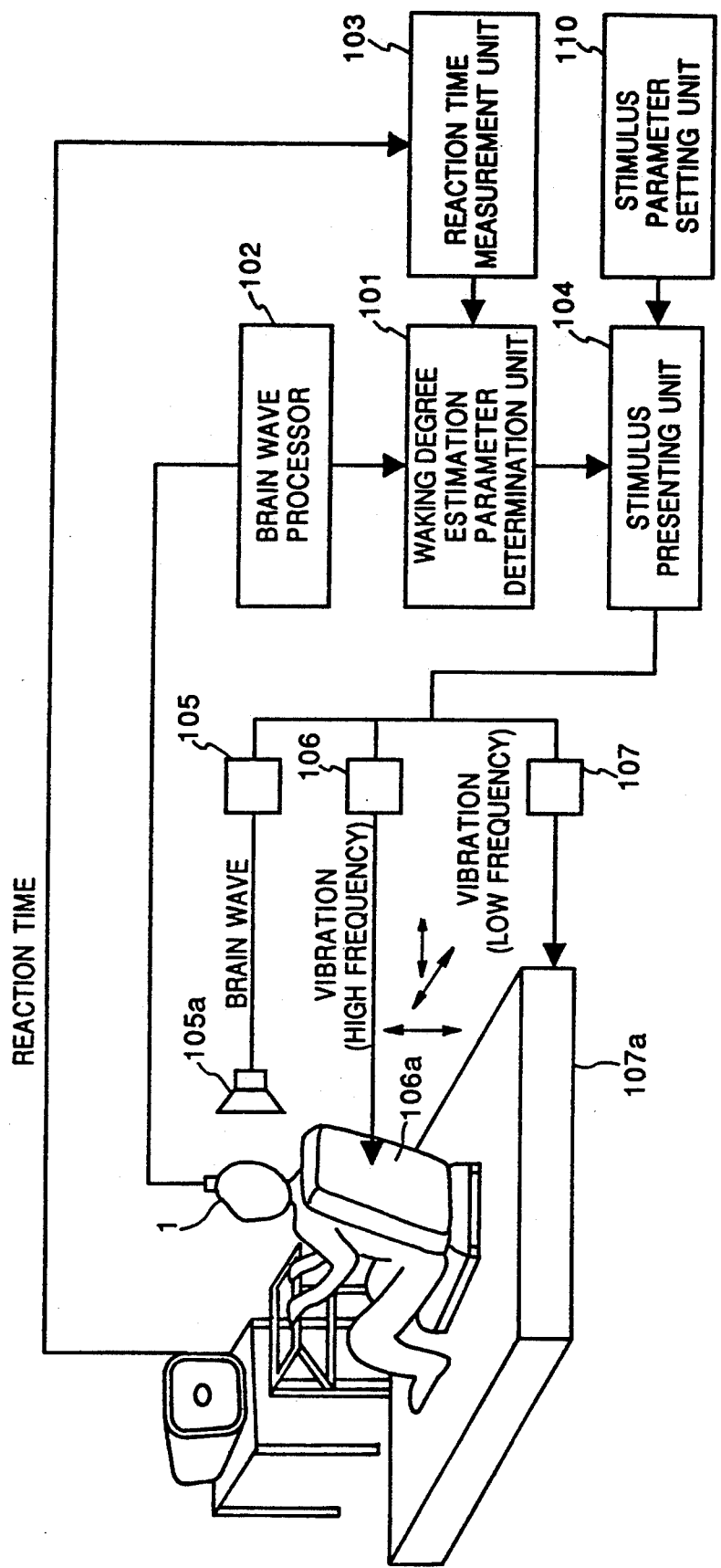

FIG. 13 is a block diagram showing an arrangement of the awakening stimulus setting device.

This awakening stimulus setting device determines a type of stimulus and a presentation method of the determined stimulus, which are most suitable for a person, since the stimulus for obtaining an awakening effect may individually vary. In this device, a brain wave processor 102, a reaction time measurement unit 103, and a waking degree estimation parameter determination unit 101 except for a stimulus presenting unit 104 and a stimulus parameter setting unit 110 have the same functions as that of the waking degree maintaining apparatus shown in FIG. 3, and a detailed description thereof will be omitted.

In FIG. 13, the subject 1 is instructed to perform a selective reaction work, and brain waves at that time are simultaneously recorded. The waking degree estimation parameter determination unit determines parameters based on the obtained reaction time and brain waves, and estimates the waking degree. When the subject is evaluated by the waking degree estimation parameter determination unit 72 of the waking degree maintaining apparatus shown in FIG. 3 prior to evaluation of this device, the waking degree can be immediately estimated.

In the stimulus parameter setting unit 110, the types of stimulus and their presentation methods for determining an optimal stimulus state are temporarily set. When it is determined that the waking degree of the subject 1 has dropped, the stimulus presenting unit 104 causes a loudspeaker driver 105 to generate a tone from a loudspeaker 105a, causes a vibration driver 106 to vibrate a seat 106a incorporating a vibrator at a high frequency, or causes a vibration driver 107 to vibrate a vibrating device 107a at a low frequency according to the data set in the stimulus parameter setting unit 110, thereby presenting a stimulus to the subject 1. The waking degree of the subject is estimated based on brain waves obtained when the stimulus is presented, and the estimated waking degrees before and after the stimulus is presented are compared to check if an effect is obtained.

By changing the stimulus state and the type of stimulus, a stimulus most effective for waking control can be selected. Furthermore, the waking state of a person can be maintained based on the obtained result, thus obtaining the waking control effect.

<Interpretation of Estimated Waking Degree>

Figure 14:
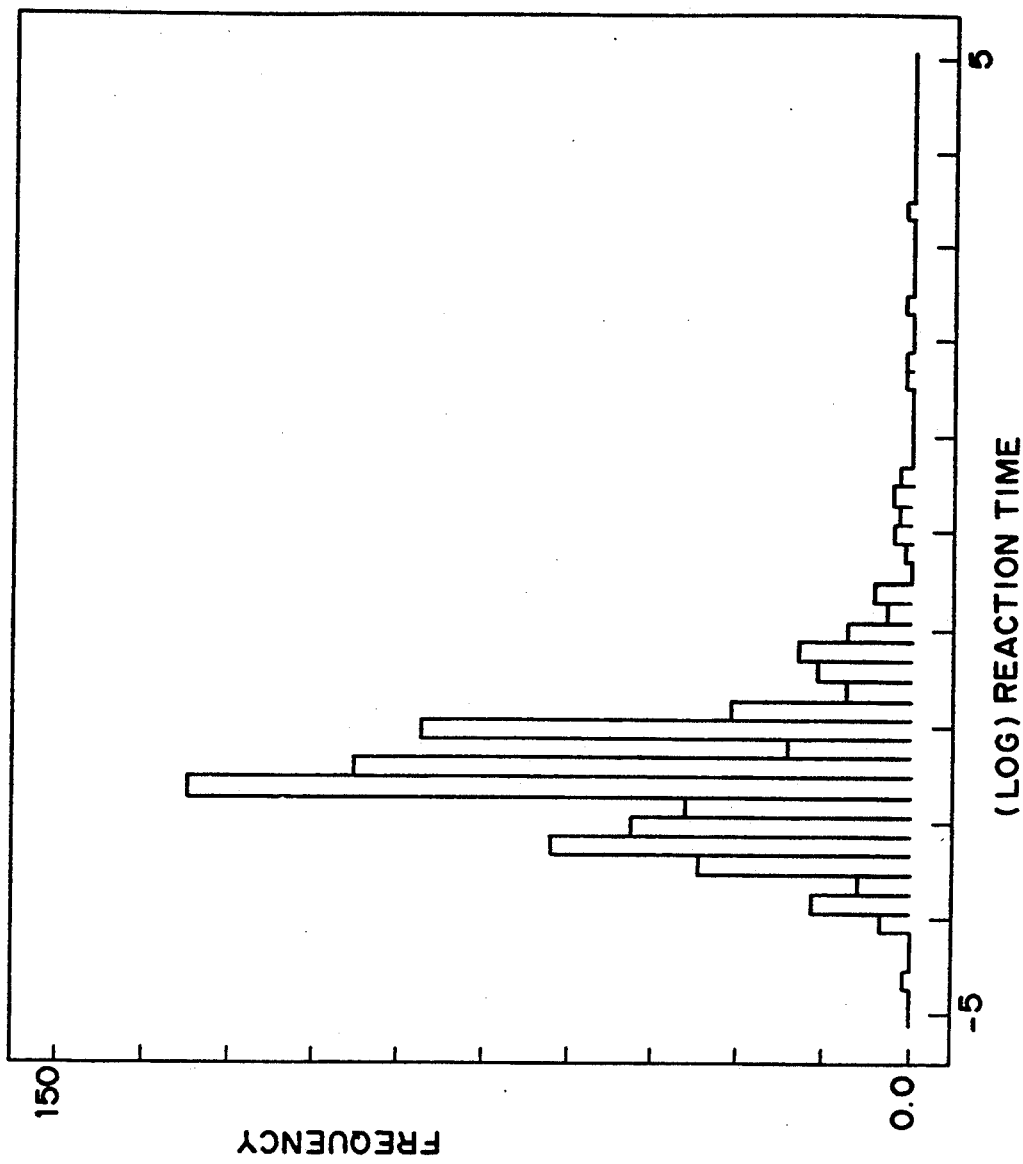
Figure 15:
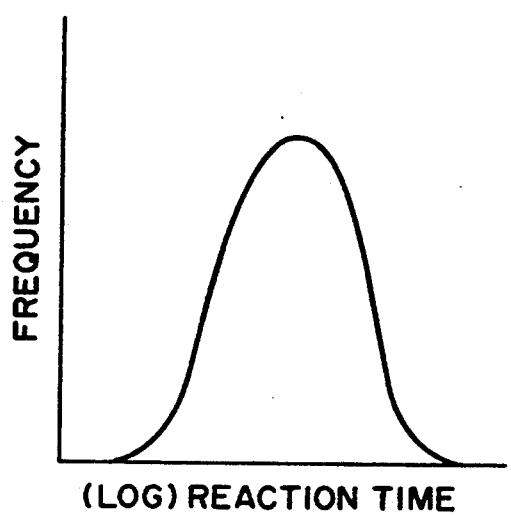

When the reaction time is measured for a long period of time to obtain its distribution, the distribution graph shown in FIG. 14 is obtained. In the distribution shown in FIG. 14, the (logarithmic) reaction time is plotted along the abscissa, and the frequency is plotted along the ordinate. The distribution is slightly distorted as a figure since the sampling intervals on the abscissa are short. When the sampling intervals and the number of points of data are changed, this distribution is approximated to the normal distribution shown in FIG. 15. In FIG. 15, the right end side of the graph corresponds to a sleepy state, and the left end side corresponds to a waking state.

Figure 16:
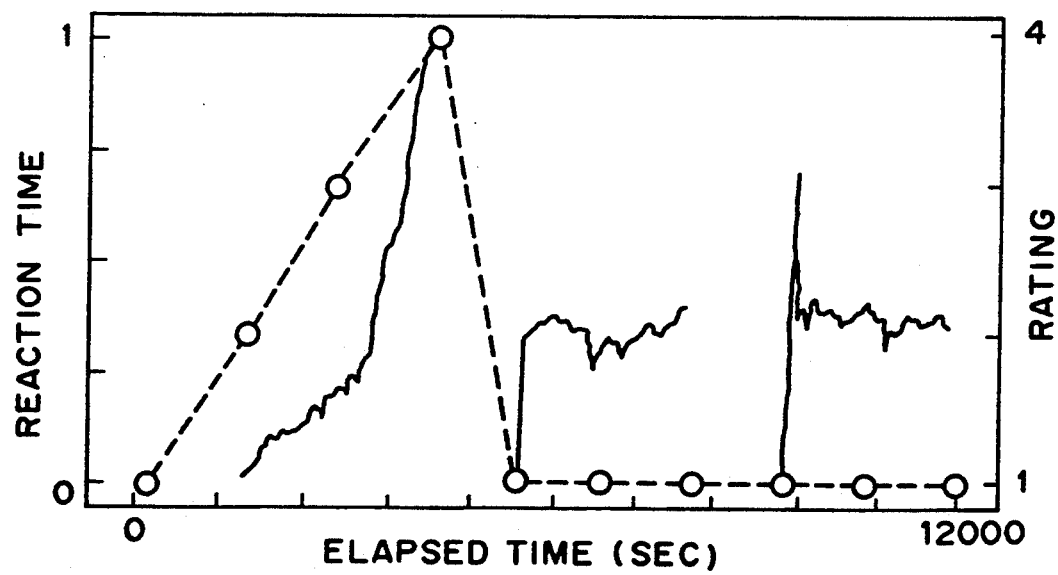

FIG. 16 shows a comparison result between the time change pattern of the reaction time and the time change pattern of sleepiness (waking degree). As can be seen from FIG. 16, the time change pattern of the reaction time (solid curve in FIG. 16) and the subjective symptom of sleepiness (broken curve in FIG. 16) have similar change tendencies, and it can be interpreted that the reaction time value corresponds to the waking degree. The subjective symptom of sleepiness is plotted according to the report based on the memory of the subject after the experiments.

Figure 17:
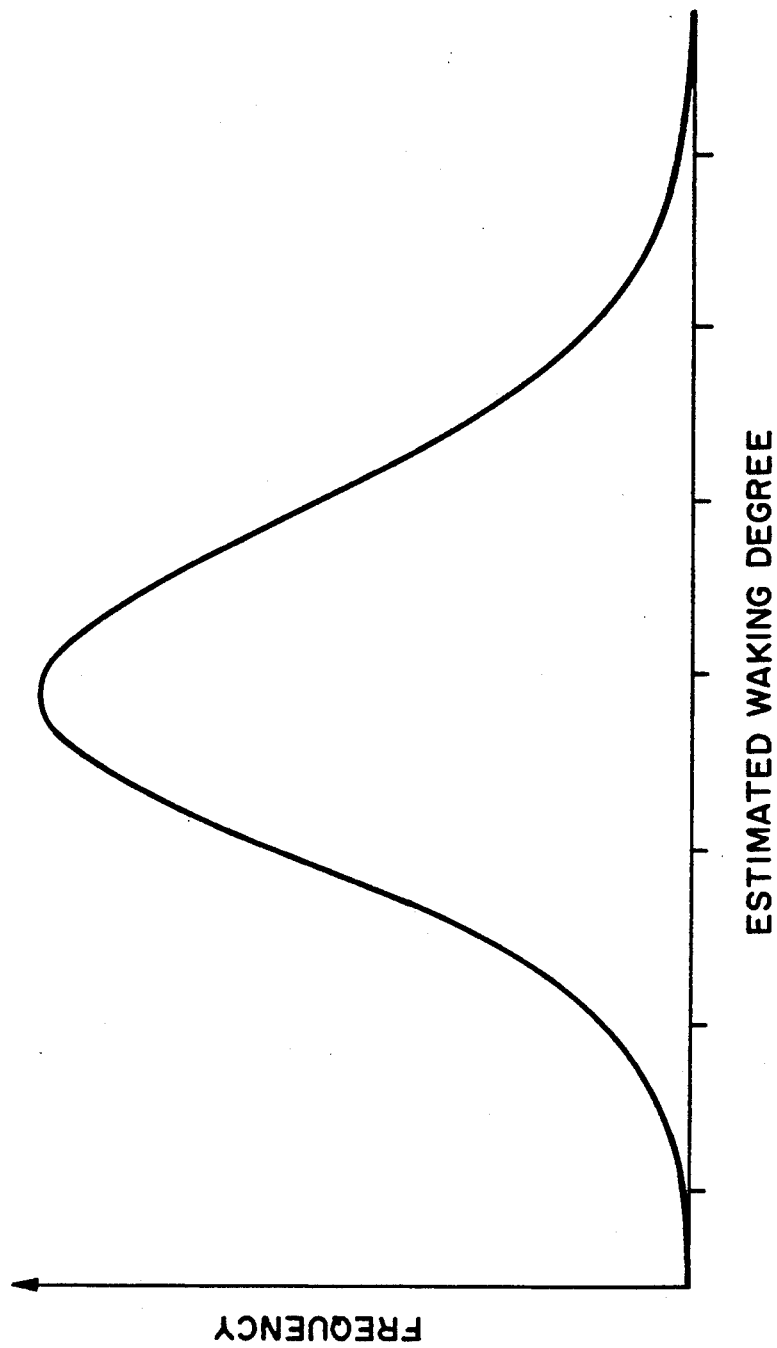

It can be interpreted that the estimated value of the reaction time estimated using equation (1) corresponds to the estimated value of the waking degree, and it can also be interpreted that the distribution of the reaction time corresponds to the distribution of the estimated waking degree. Thus, a biological feedback reference value to be described below is set on the basis of the distribution of the estimated waking degree shown in FIG. 17.

<Setting of Biological Feedback Reference Value>

Figure 18:
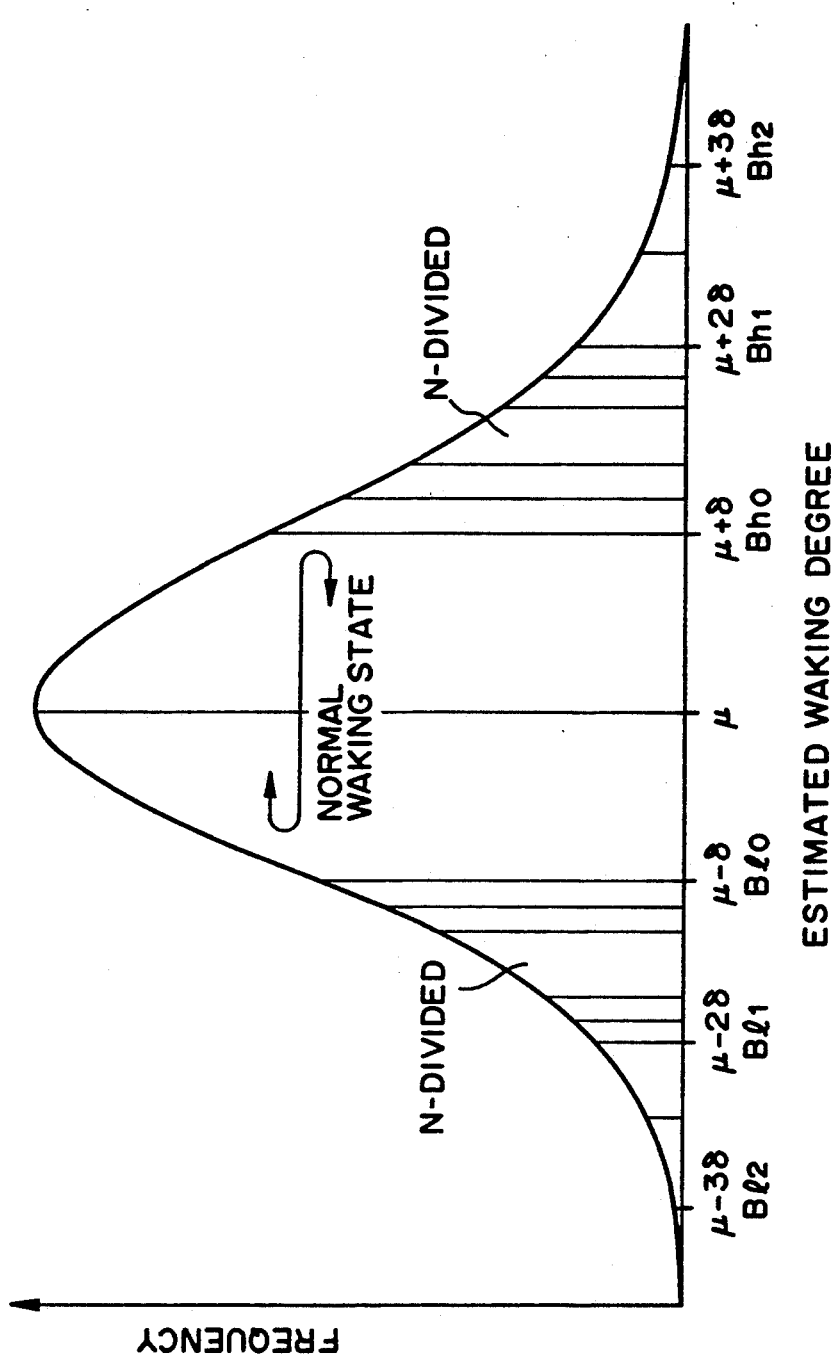
FIGS. 18 to 23 are views for explaining a method of setting a biological feedback reference value according to the embodiment.

FIG. 18 is a view for explaining a method of setting a biological feedback reference value using the estimated waking degree.

When a statistically sufficient number of estimated waking degrees are collected, it is expected that the distribution of the estimated waking degrees becomes a normal distribution, as indicated by a solid curve in FIG. 18.

In general, in the normal distribution, if the average value of the distribution is represented by $\mu$, and the standard deviation is represented by $\sigma$, values falling within a range between $\mu - a$ and $\mu + a$ are interpreted as errors from the average, and values equal to or larger than $\mu + a$ or equal to smaller than $\mu - a$ are considered as abnormal values which do not belong to this distribution. "a" assumes $\sigma$ or $2\sigma$. In this case, a biological feedback reference value is set by adopting this principle.

$\mu$ assumes an average value of reaction times obtained by previous experiments, and $\sigma$ assumes a standard deviation of the reaction times. When the estimated waking degree falls within a range between $\mu - a$ and $\mu + a$, it is considered that the waking degree falls within the range of a normal waking state, and no stimulus is presented to the driver. In this case, $a = \sigma$ is normally set. However, since the stimulus presentation start timing varies depending on the physiological characteristics of each individual, a value matching with the characteristics of a person of interest may be set. In FIG. 18, $Bh_0 (= \mu + \sigma)$ is the upper limit value of the normal waking state, and $B\lambda_0 (= \mu - \sigma)$ is the lower limit value of the normal waking state.

<Reference Value in Low Waking Degree State>

The principle of setting the biological feedback reference value in the low waking degree state will be explained below.

When the estimated waking degree exceeds $Bh_0$, this means that the reaction time is becoming abnormally long. Thus, it is determined that the waking degree is beginning to drop, and presentation of an awakening stimulus is started. $Bh_1$ is a threshold value which allows to determine that the subject is in an extremely low waking degree state. This value is normally given by $Bh_1 = \mu + 2\sigma$, and the setting value is changed according to the individual differences, as described above.

When the estimated waking degree falls within a range between $Bh_0$ and $Bh_1$, a driver is not conscious of sleepiness yet although the tendency of a drop in waking degree begins to appear. When the estimated waking degree falls within this range, the waking effect can be obtained by positively presenting a stimulus. For this reason, an exciting stimulus is presented in this range.

When the estimated waking degree exceeds $Bh_1$, it is considered that the driver is conscious of sleepiness. When the estimated waking degree exceeds $Bh_2$, it is considered that the waking degree has further dropped, i.e., the driver is driving half asleep. When the estimated waking degree falls within the range between $Bh_1$ and $Bh_2$, the driver must be awakened by presenting a considerable stimulus, or composite stimuli of a tone, a vibration, a smell, and an air blowing amount of an air conditioner. Note that the values $Bh_1$ and $Bh_2$ are respectively $\mu + 2\sigma$ and $\mu + 3\sigma$. However, these values are also set according to the physiological characteristics of a person (driver) of interest.

When the waking degree drops further, and the estimated waking degree exceeds $Bh_2$, an alarm for stopping the driving operation is generated to the driver.

Figure 19:
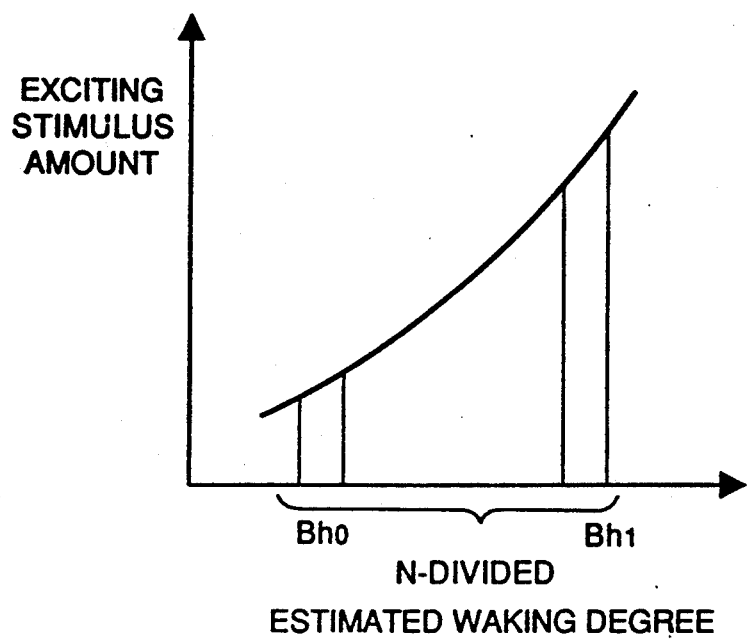

As described above, when the estimated waking degree falls within the range between $Bh_0$ and $Bh_1$, this range is divided into N ranges, as shown in FIG. 18, and the stimulus amount is increased according to the degree of a drop in waking degree to obtain an exciting effect so as to enhance the waking effect. In this case, the tone volume or the magnitude of acceleration of the vibration may be used as a stimulus. FIG. 19 shows the relationship between the exciting stimulus amount given to the driver and the estimated waking degree at that time.

<Reference Value in Strained (Excited) State>

The principle of setting the biological feedback reference value in an excited state will be explained below.

In FIG. 18, when the estimated waking degree is decreased below $B\lambda_0$, this means that the reaction time is becoming abnormally short. Thus, it is determined that the driver is beginning to be strained (over-concentrated), and presentation of a calming stimulus is started.

In FIG. 18, $B\lambda_1$ is a threshold value which allows to determine that a driver is under an extreme strain, and this value is normally given by $B\lambda_1 = \mu - 2\sigma$. For the same reason as above, the setting value of this value is changed according to the individual differences.

Within a range between $B\lambda_0$ and $B\lambda_1$, the driver is not conscious of an extreme strain, e.g., a strain causing a panic yet although the strain tendency begins to physiologically appear. Therefore, when the estimated waking degree falls within this range, it is considered that the effect of calming the strain can be obtained by positively presenting a stimulus. Thus, a calming stimulus is presented in this range.

When the estimated waking degree drops below $B\lambda_1$, the driver is conscious of a strain. When the estimated waking degree drops further below $B\lambda_2$, it is considered that the waking degree drops further, i.e., the driver is driving half asleep. When the estimated waking degree falls within the range between $B\lambda_1$ and $B\lambda_2$, the driver must be awakened by presenting a considerable calming stimulus, or composite stimuli of a tone, a vibration, a smell, and an air blowing amount of an air conditioner. Note that the values $B\lambda_1$ and $B\lambda_2$ are respectively $\mu - 2\sigma$ and $\mu - 3\sigma$. However, these values are also set according to the physiological characteristics of each driver.

When the waking degree drops further, and the estimated waking degree drops below $B\lambda_2$, an alarm for stopping the driving operation is generated to the driver.

Figure 20:
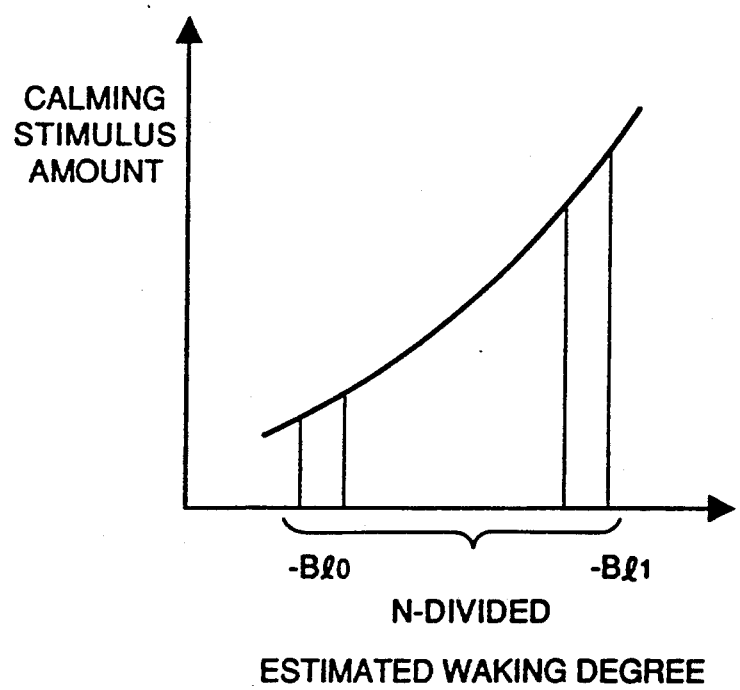

As described above, when the estimated waking degree falls within the range between $B\lambda_0$ and $B\lambda_1$, this range is divided into N ranges, as shown in FIG. 18, and the stimulus amount is increased according to the degree of a drop in waking degree to enhance the calming effect. In this case, the 1/f fluctuation music, smell, warm wind, or the like may be presented as a stimulus. FIG. 20 shows the relationship between the calming stimulus amount given to the driver and the estimated waking degree at that time.

Processing for setting the biological feedback reference value and processing for coping with a low waking degree state or an over-strained state will be described below with reference to the flow charts.

Figure 21:
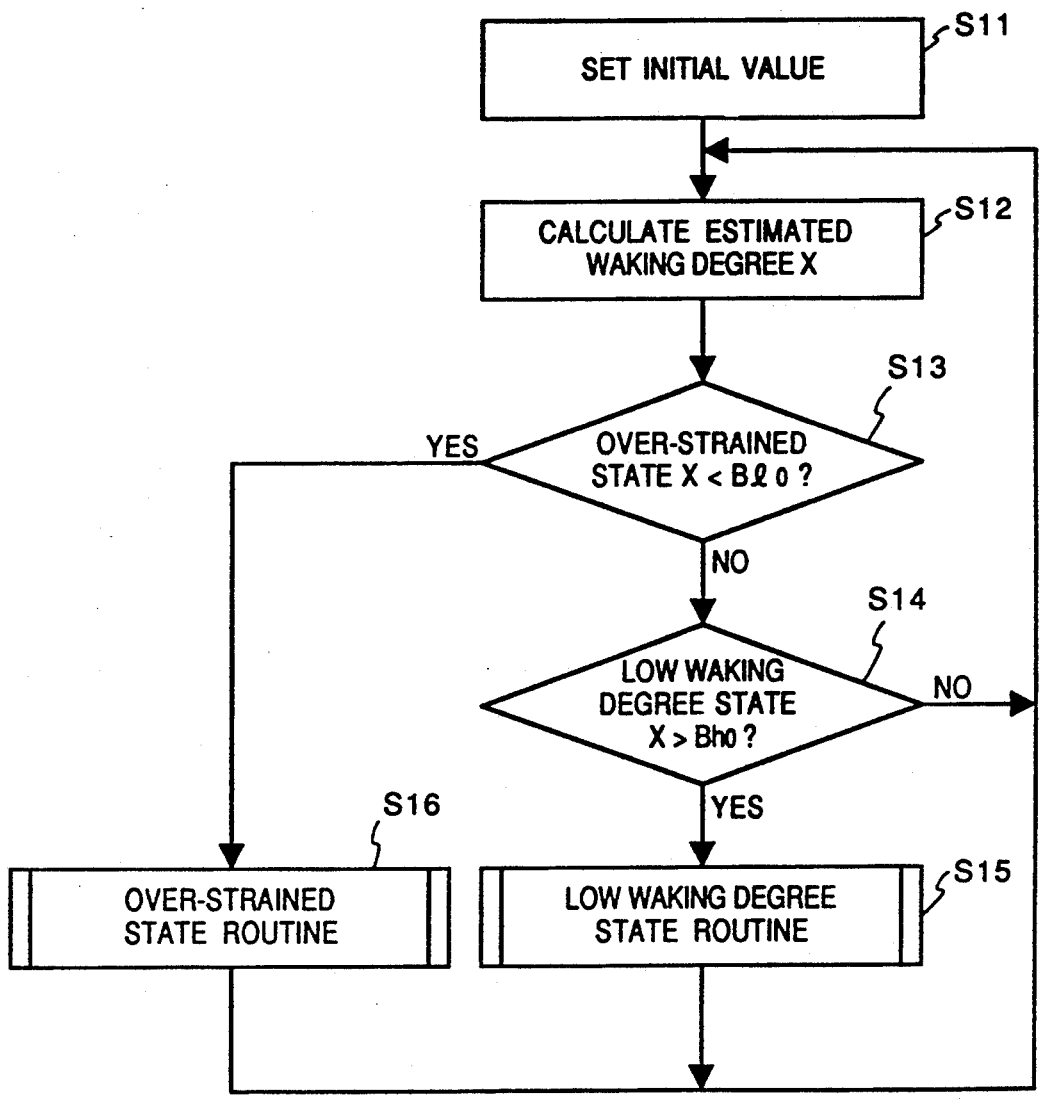

FIG. 21 is a flow chart showing processing for setting the biological feedback reference value. In FIG. 21, an initial value for setting the reference value is set in step S11. In step S12, an estimated waking degree X is calculated by the above-mentioned method. In step S13, it is checked if the estimated waking degree X calculated in step S12 is smaller than $B\lambda_0$. If $X < B\lambda_0$, i.e., if an over-strained state is determined, the flow advances to step S16, i.e., an over-strained state routine.

However, if NO in step S13, it is checked in step S14 if the estimated waking degree X is larger than $Bh_0$, i.e., if a driver is in a low waking degree state. If $X > Bh_0$, it is determined that the waking degree is beginning to drop, and the flow advances to step S15 (low waking degree state routine).

Figure 22:
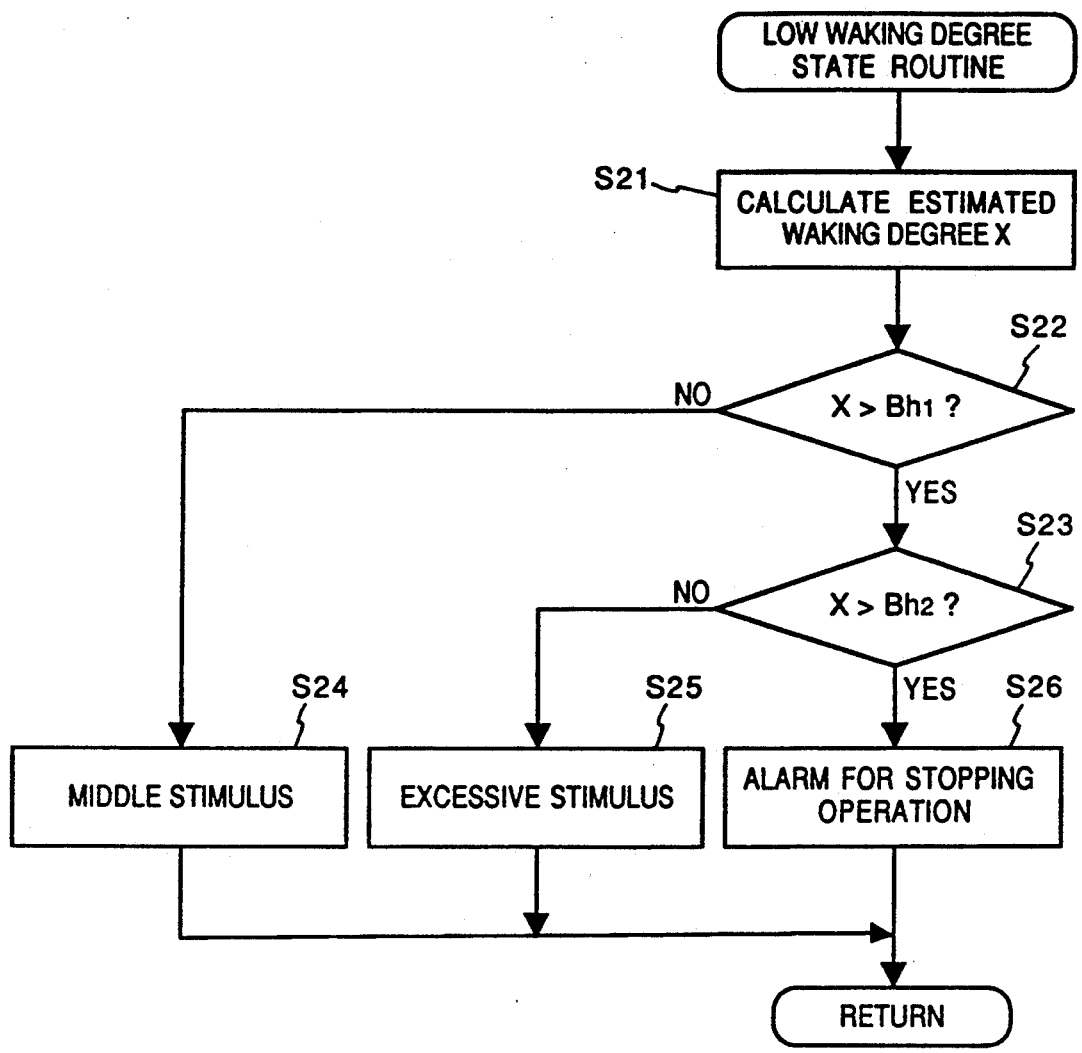

FIG. 22 is a flow chart showing the low waking degree state routine. In FIG. 22, in step S21, the estimated waking degree X is calculated by the above-mentioned method. In step S22, it is checked if the degree X is larger than $Bh_1$. If $X \leq Bh_1$, a middle stimulus is given in step S24.

If YES in step S22, it is determined that the driver is conscious of sleepiness, and the flow advances to step S23 to check if the estimated waking degree exceeds $Bh_2$.

If NO in step S23, an excessive stimulus is given in step S25; otherwise, it is determined that the estimated waking degree exceeds $Bh_2$, and an alarm for stopping the driving operation is generated to the driver in step S26.

Figure 23:
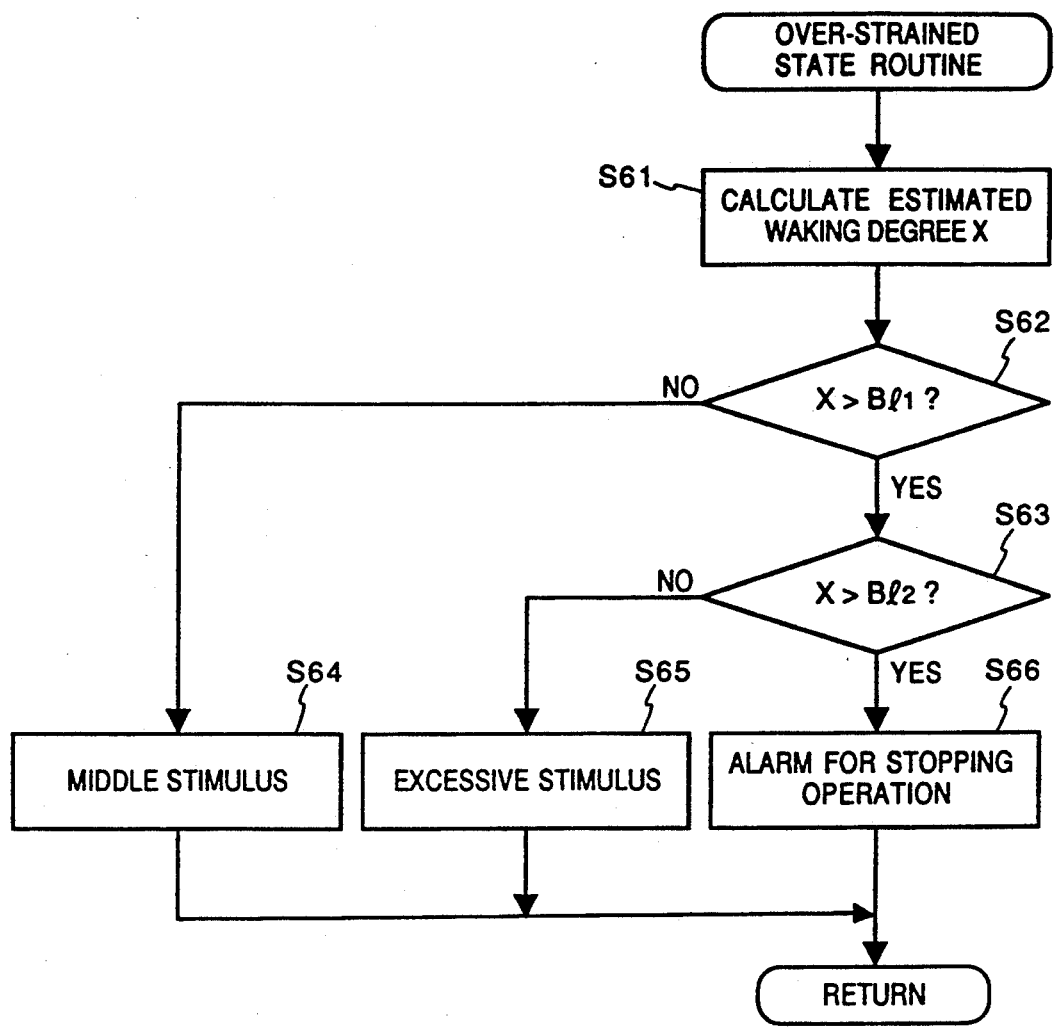

FIG. 23 is a flow chart showing the over-strained state routine. In FIG. 23, the estimated waking degree X is calculated by the above-mentioned method in step S61. In step S62, it is checked if the degree X is smaller than $B\lambda_1$. If $X \geq B\lambda_1$, a middle calming stimulus is given in step S64.

If YES in step S62, it is determined that the driver is conscious of a strain, and the flow advances to step S63 to check if the estimated waking degree is smaller than $B\lambda_2$.

If NO in step S63, an excessive calming stimulus is given in step S65; otherwise, it is determined that the estimated waking degree is decreased below $B\lambda_2$, and an alarm for stopping the driving operation is generated to the driver in step S66.

A method of detecting a drop in waking degree on the basis of the rhythm of the waking degree, especially, the disorder of the waking rhythm will be described below.

<Rhythm Characteristics of Waking Degree>

First, a phenomenon in which the rhythm of the waking degree appears will be described below with reference to experimental data associated with the reaction time.

The reaction time and the waking degree have a positive correlation therebetween, as described above, and the estimated waking degree and the reaction time have a quantitatively high correlation therebetween. In other words, since the reaction time can be estimated with high precision based on the estimated waking degree, to explain the rhythm characteristics of the waking degree using reaction time data is synonymous with to explain the characteristics about the estimated waking degree.

Figure 24:
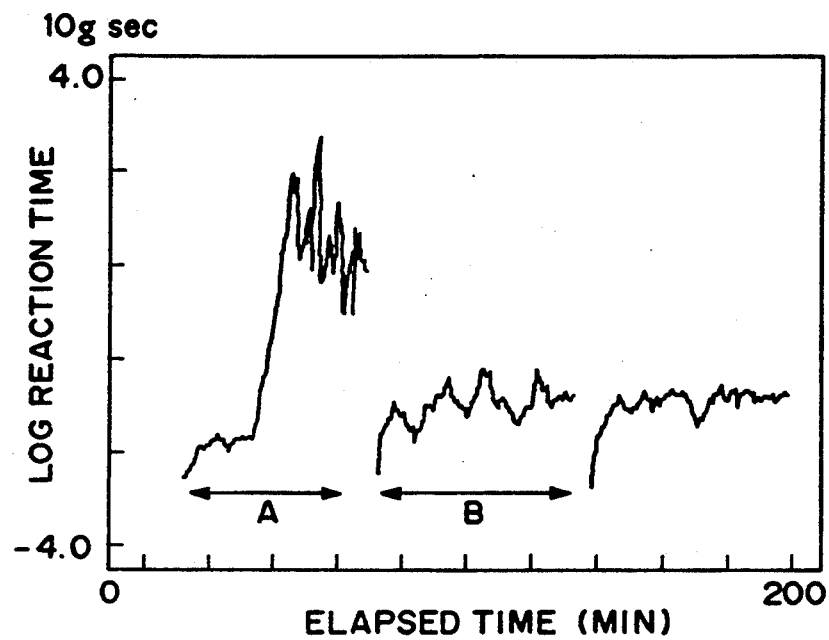

FIG. 24 is a graph showing the measurement result of the reaction time over a long period of time. The elapsed time is plotted along the abscissa, and the LOG-converted reaction time is plotted along the ordinate. Note that a division between adjacent data on the graph represents a break time (5 minutes) given to the subject.

In a region B in FIG. 24, the reaction time varies at a regular period, and the curve in region B represents the typical characteristics in an awake state. More specifically, even in the awake state, the waking degree of a person varies within a range that does not cause interference of his or her work, and the variation has a regular period.

In contrast to this, a region A represents that the subject is in a sleeping state. More specifically, in an early stage of the region A, the subject is in a normal waking state, but in the latter stage, he or she causes an abrupt drop in waking degree, and falls into a doze. As can be seen from FIG. 24, the reaction time in this state is extremely long.

In summary, upon comparison between the reaction times in the regions A and B in FIG. 24, the waking rhythm exists in the normal waking state, but when the waking degree drops, the rhythm disappears. By utilizing this fact, the reference value for stimulus presentation in biological feedback control is set.

Figure 25:
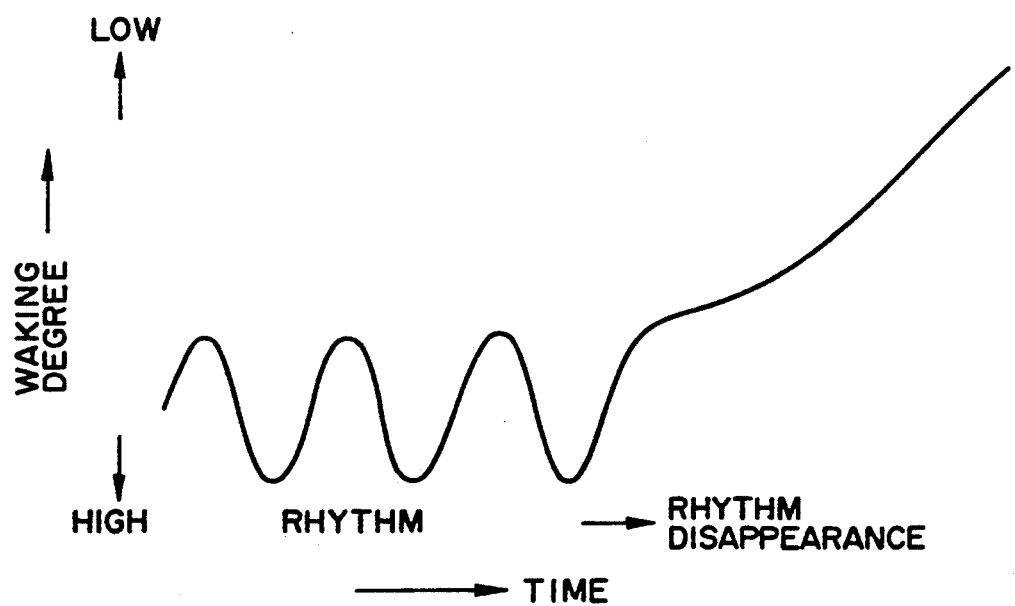

FIG. 25 illustrates the rhythm of the waking degree and a state until the rhythm disappears. As can be seen from FIG. 25, the waking degree has two states. That is, in one state, the waking degree rhythmically changes, and in the other state, the rhythm disappears in a direction to decrease the waking degree. As described above, the waking rhythm is periodical, but has a "fluctuation" because it is a human's rhythm. The "fluctuation" is defined by the following concept.

Figure 26:
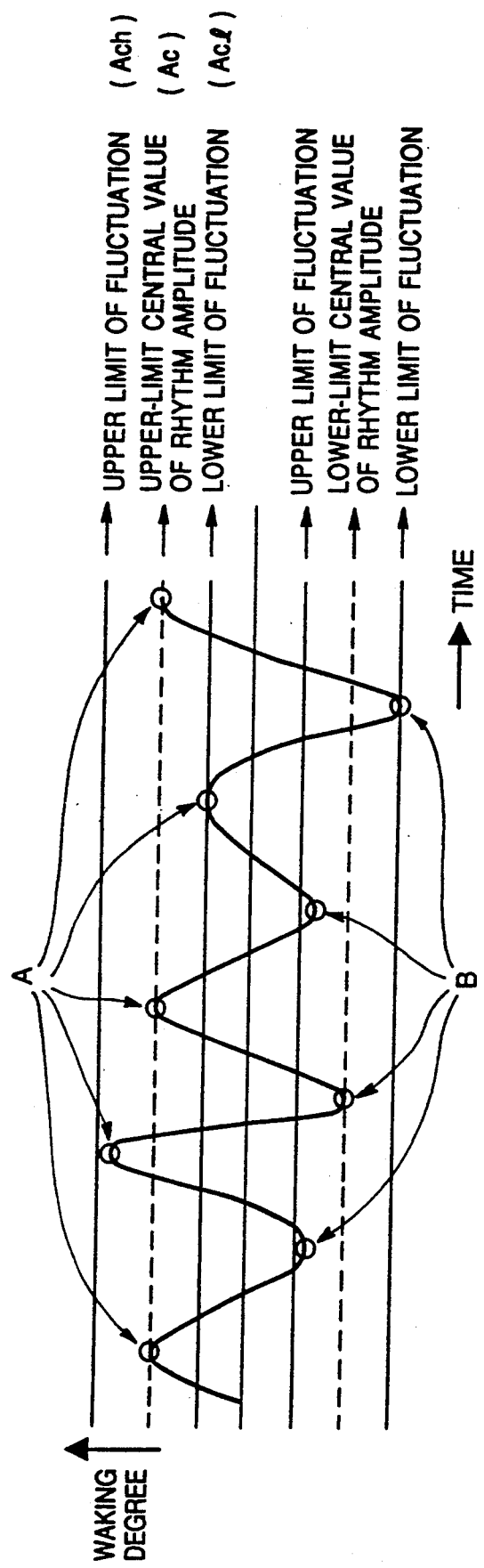
Figure 27:
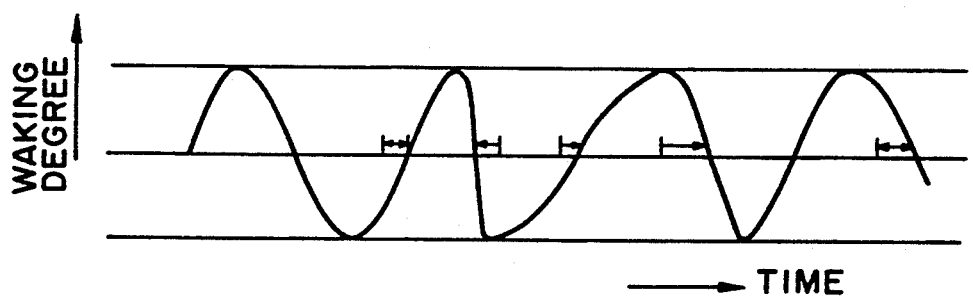

The "fluctuation" includes a fluctuation of the rhythm amplitude and a fluctuation of the period. FIG. 26 shows a fluctuation of the waking amplitude in which the waking degree varies although the period is constant. FIG. 27 shows a case wherein the period of the waking rhythm fluctuates while the amplitude is constant.

The practical waking rhythm appears as a phenomenon including the fluctuations of both the amplitude and period. For this reason, upon detection of the waking rhythm, the amplitude period of the rhythm and its fluctuation width, and the average period of the rhythm and its periodic fluctuation width must be obtained for a target subject in advance.

<Parameters of Waking Rhythm Characteristics>

A method of obtaining parameters representing the waking rhythm characteristics of each individual will be explained below.

In this case, a reference value of the rhythm applies to only the beginning of a drop in waking degree since it is not suitable for applying the rhythm characteristics to detection of an over-strained state. That is, in experimental data, the disorder phenomenon of the rhythm toward a drop in waking degree clearly appears. However, in the over-strained state, since the reaction time saturates at a predetermined value, a specific phenomenon, i.e., the disorder of the rhythm, does not appear.

<Calculation of Fluctuation of Waking Rhythm Amplitude>

FIG. 28 is a flow chart showing a method of calculating the fluctuation of the waking rhythm amplitude. In FIG. 28, in step S71, time-series data of the measured reaction time or time-series data of the estimated waking degree is read out. In step S72, sufficient smoothing of the time-series waveform is performed, thereby smoothing the waveform and removing noise. This smoothing processing is to extract only waveform components associated with the waking rhythm since the time-series waveform includes noise and irregularly fluctuating components. In this case, the degree of smoothing is determined not to lose the rhythm characteristics.

In step S73, the number N of times of measurements for detecting peak values of the waking degree amplitude is initialized. In step S74, the peak value is detected, and N is updated, i.e., the value N is incremented by 1. In this case, only peaks from which the waking degree tends to drop (peaks A in FIG. 26) are detected. The opposing peaks, i.e., peaks B in FIG. 26 represent a strain limit.

In step S75, the obtained peak value is stored in a memory. In step S76, it is checked if the next time-series data from which a peak is to be detected is present. If YES in step S76, the flow returns to step S74 to continue detection of the peak value.

However, if NO in step S76, various calculations according to the following equations are performed in step S77.

As a method of detecting the peak value in step S74, a method of obtaining a differential coefficient at a detection point, and determining, as a peak value, the differential coefficient which is inverted from positive to negative is adopted.

As the equations in step S77, an average peak value Ap of the waking degree amplitude is given by:

$$Ap = \frac{1}{N} \sum_{i=1}^{N} P(i) \quad (2)$$

A standard deviation A of the waking degree amplitude is given by:

$$A\sigma = \sqrt{\frac{1}{N} \sum_{i=1}^{N} (P(i) - Ap)^2} \quad (3)$$

A low waking degree reference value A is given by:

$$A\lambda = Ap + X \cdot A\sigma \quad (1 < X < 3) \quad (4)$$

Aλ calculated in this manner becomes a reference value which allows to determine that a drop in waking degree is beginning to appear.

<Judgment of Drop in Waking Degree From Waking Rhythm Amplitude>

Figure 29:
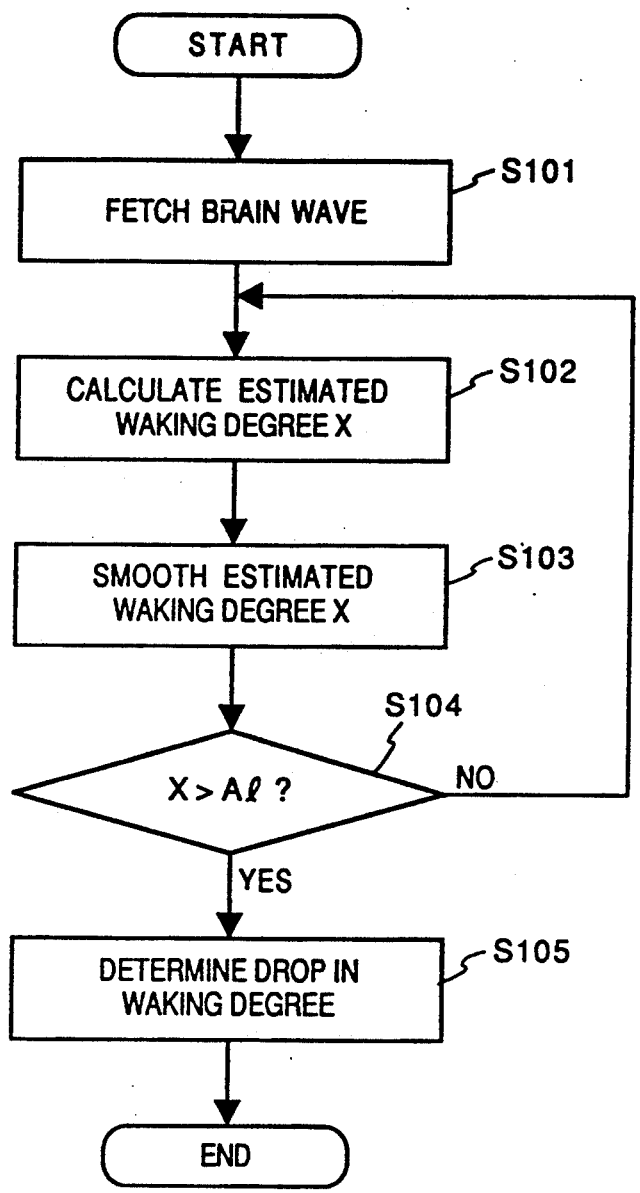

FIG. 29 is a flow chart for discriminating the beginning of a drop in waking degree on the basis of the low waking degree reference value Aλ obtained by the above-mentioned equations. In step S101 in FIG. 29, the brain waves of a driver are fetched by the above-mentioned method, and in step S102, the estimated waking degree X is calculated. In this case, since the estimated waking degree is calculated by the same method as that described above, a detailed description thereof will be omitted.

The time-series data of the estimated waking degree calculated in step S102 include both components representing the rhythm and noise components. In step S103, the time-series data is averaged using several points of previously obtained estimated waking degrees, thereby removing the noise components. In step S104, the estimated waking degree X is compared with the low waking degree reference value Aλ previously obtained by equation (4) to check if X > Aλ is satisfied.

If YES in step S104, the flow advances to step S105, and it is determined that a drop in waking degree is beginning to appear.

<Calculation of Fluctuation of Waking Rhythm Period>

In order to obtain the period of the waking rhythm, a base value of the waking degree amplitude is initially calculated. The base value means a reference value (shift amount) with reference to which the waking degree oscillates with regular upper and lower amplitudes within a range of the fluctuation of the amplitude.

In order to obtain the base value of the waking degree amplitude, the upper- and lower-limit peaks of the waking degree are obtained. Of these peaks, since the upper-limit peaks are obtained by the same processing sequence as that shown in the flow chart of FIG. 28, a detailed description thereof will be omitted.

Figure 30:
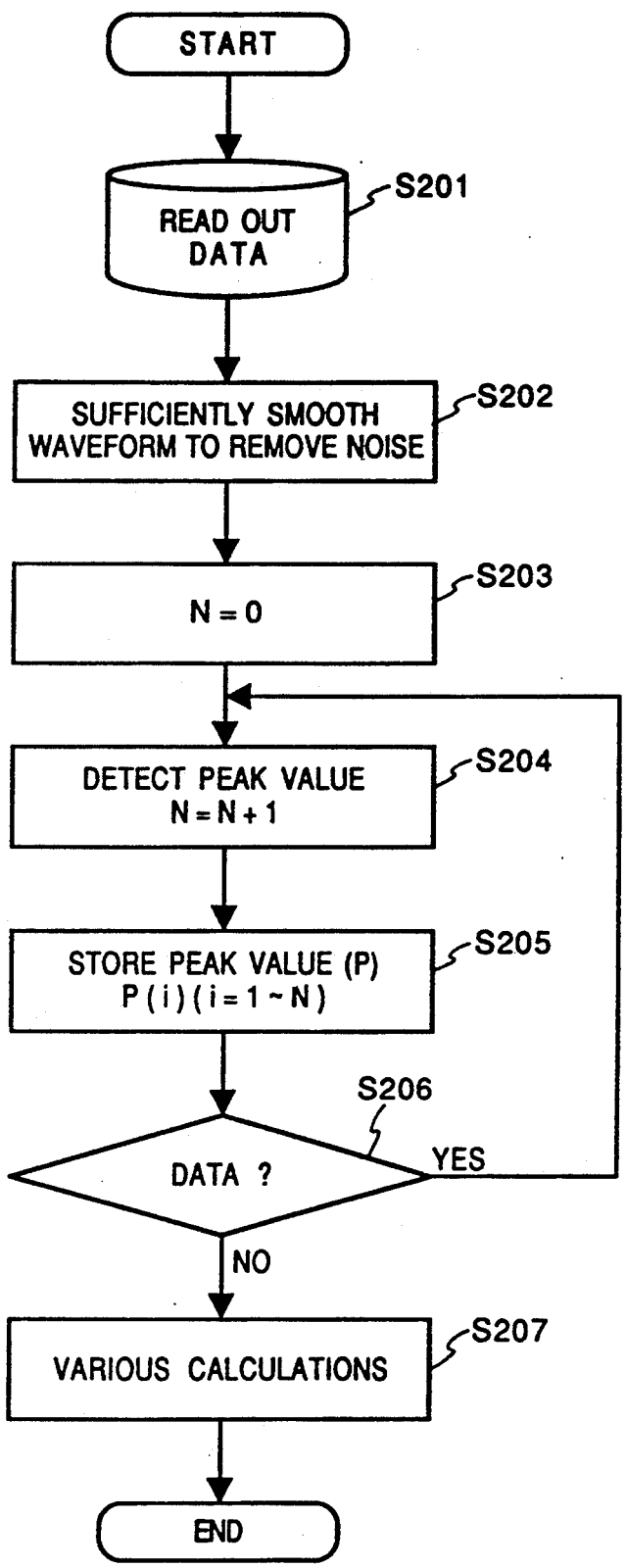

FIG. 30 is a flow chart showing processing for obtaining the lower-limit peaks of the waking degree, and this flow chart is basically the same as that for obtaining the upper-limit peaks. More specifically, in step S201 in FIG. 30, time-series data of the measured reaction time or the estimated waking degree is read out. In step S202, sufficient smoothing of the time-series waveform is performed, thereby smoothing the waveform and removing noise.

In step S203, the number N of times of measurements is initialized. In step S204, the peak value is detected, and the value N is updated. In step S205, the obtained peak value is stored in a memory, and in step S206, it is checked if the next time-series data from which a peak is to be detected is present. If YES in step S206, the flow returns to step S204 to continue detection of the peak value. However, if NO in step S206, various calculations according to the following equations are performed in step S207.

A lower-limit average peak value Bp of the waking degree amplitude is given by:

$$Bp = \frac{1}{N} \sum_{i=1}^{N} P(i) \quad (5)$$

A standard deviation B of the waking degree amplitude is given by:

$$B\sigma = \sqrt{\frac{1}{N} \sum_{i=1}^{N} (P(i) - Bp)^2} \quad (6)$$

A value ½ the sum of the obtained upper- and lower-limit peaks is used as a base value CO of the waking degree amplitude. That is, CO is given by:

$$CO = (Ap + Bp)/2 \quad (7)$$

Note that the above-mentioned processing is premised on a condition that the amplitude of the waking degree regularly changes upward and downward with reference to the base value.

Figure 31:
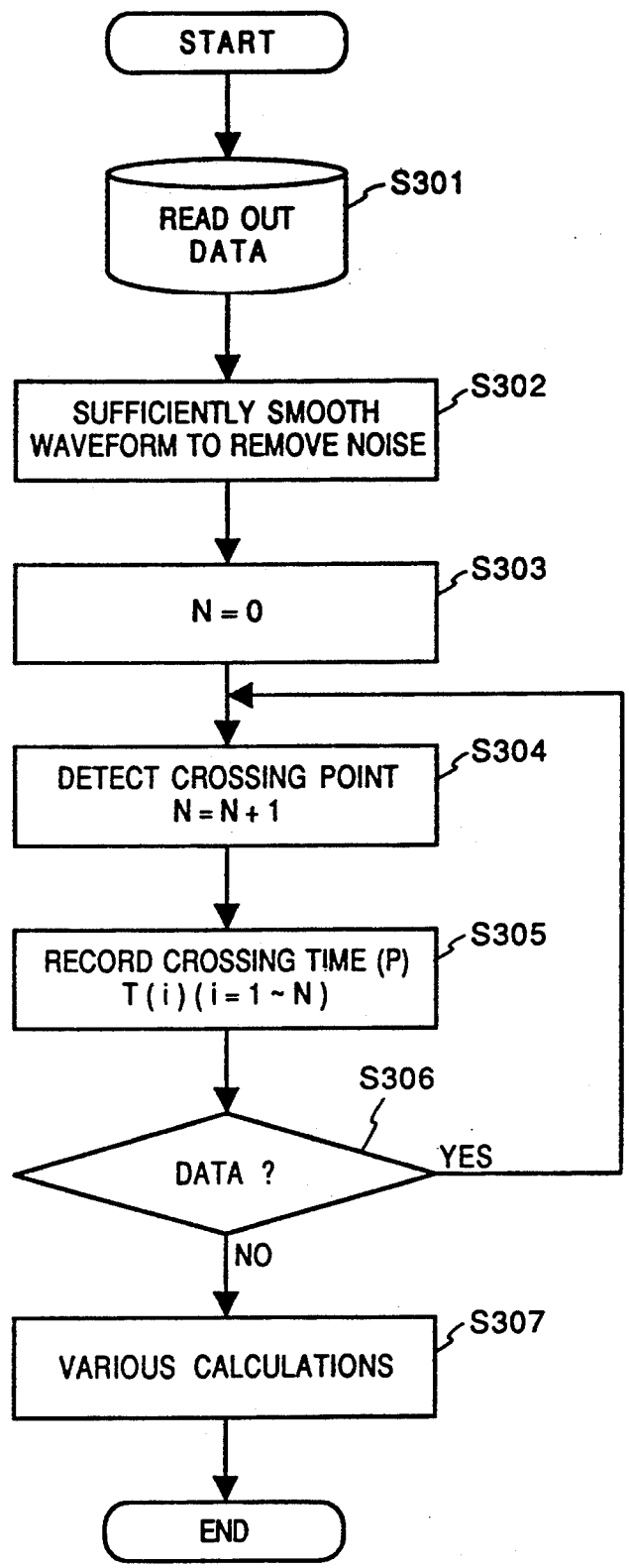

FIG. 31 is a flow chart showing a method of calculating the period of the waking rhythm. In FIG. 31, in step S301, time-series data of the measured reaction time or the estimated waking degree is read out. In step S302, sufficient smoothing of the time-series waveform is performed, thereby smoothing the waveform and removing noise. This smoothing processing is to extract only waveform components associated with the waking rhythm since the time-series waveform includes noise and irregularly fluctuating components. In this case, the degree of smoothing is determined not to lose the rhythm characteristics.

Figure 32:
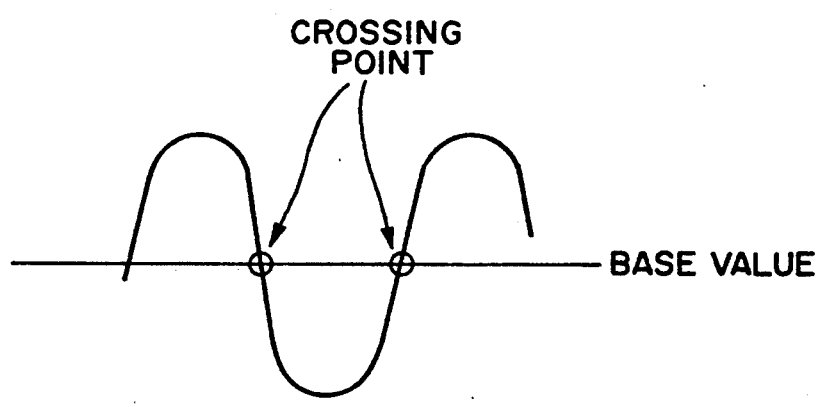

In step S303, the number N of times of measurements for detecting crossing points (see FIG. 32) of the base value is initialized. In step S304, the crossing point of the base value is detected, and the value N is incremented by N = N + 1. The crossing point means a point when values X − CO and X′ − CO have different signs where X is the current estimated waking degree, and X′ is the estimated waking degree of immediately preceding data. In other words, the crossing point is a point where the estimated waking degree crosses the base value.

In step S305, a detection time of the crossing point (crossing time) is stored in a memory. In step S306, it is checked if the next time-series data from which a crossing point is to be detected is present. If YES in step S306, the flow returns to step S304 to continue detection of the crossing point. When the detected crossing time is represented by T(i) (i = 1 to N), T(i) − T(i-1) corresponds to ½ the waking rhythm.

On the other hand, if NO in step S306, various calculations according to the following equations are performed in step S307.

As the equations in step S307, an average value Ta of the period of the waking degree rhythm is given by:

$$Ta = \frac{1}{N-1} \sum_{i=2}^{N} [T(i) - T(i-1)] \quad (8)$$

A standard deviation T of the period of the waking degree rhythm is given by:

$$T\sigma = \sqrt{\frac{1}{N-1} \sum_{i=2}^{N} \{2 \cdot [T(i) - T(i-1)] - Ta\}^2} \quad (9)$$

A low waking degree reference value T is given by:

$$T\lambda = Ta + x \cdot T\sigma \quad (1 < X < 3) \quad (10)$$

Tλ obtained in this manner becomes a reference value which allows to determine that a drop in waking degree begins from the viewpoint of detection of the period of the rhythm.

<Judgment of Drop in Waking Degree from Period of Waking Rhythm>

FIG. 33 is a flow chart for discriminating the beginning of a drop in waking degree on the basis of the low waking degree reference value Tλ obtained by the above-mentioned equations. In step S401 in FIG. 33, the brain waves of a driver are fetched by the above-mentioned method. In step S402, a time T (crossing time) at which the estimated waking degree crosses the base value for the first time is stored. In step S403, the brain waves of the driver are fetched again, and in step S404, the estimated waking degree X is calculated. Since the estimated waking degree is calculated by the same method as described above, a detailed description thereof will be omitted.

In step S405, it is checked if the estimated waking degree crosses the base value later. If YES in step S405, the crossing time is stored as a new crossing time Tnew in step S407. However, if NO in step S405, the flow advances to step S406 to check if a time corresponding to half the period of the waking rhythm has elapsed from the latest crossing time.

More specifically, when the latest crossing time is represented by T, and the period concerning the fluctuation range of the rhythm period is represented by T' = T½ (= (Ta + x·Tσ)/2), the elapsed time t' from the time T is compared with T + T'. As a result if t' > T + T' is satisfied, it is determined in step S408 that a drop in waking degree is beginning to appear.

<Measurement of Blinking Frequency>

A method of measuring the blinking frequency from time-series data of the eye movement, and estimating the waking degree based on the blinking frequency will be explained below.

Figure 34:
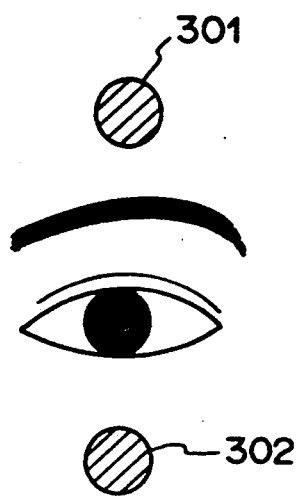
FIGS. 34 to 43 are views for explaining a measurement of the blinking frequency.
Figure 35:

FIGS. 34 and 35 show methods of measuring the eye movement of a person. In FIG. 34, living body electrodes 301 and 302 are attached to positions above and below an eyeball to detect a potential difference therebetween, and the obtained signal is amplified by a physiological signal amplifier (not shown), thereby detecting the vertical eye movement. Similarly, FIG. 35 shows a method of detecting the horizontal eye movement using living body electrodes 303 and 304.

Figure 36:
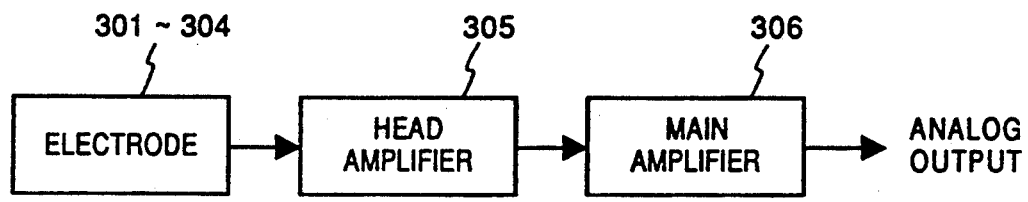
Figure 37:
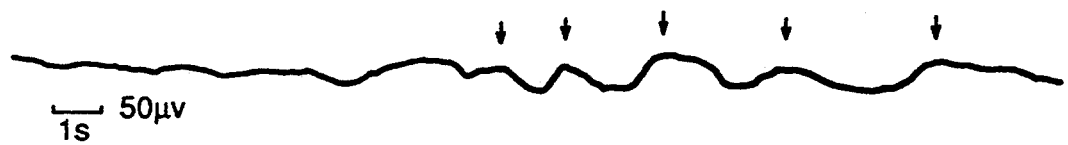

FIG. 36 is a block diagram showing a partial arrangement of a device for obtaining an eye movement signal. Signals from the electrodes 301 to 304 are output as an analog signal through a head amplifier 305 and a main amplifier 306. FIG. 37 shows a signal waveform of the eye movement obtained by the device with the above arrangement. When the eyeball moves, the potential waveform fluctuates. As can be seen from FIG. 37, the eye movement occurs at points indicated by arrows in FIG. 37. The peak levels of the waveform at these points vary depending on the magnitude of the eye movement. Note that the illustrated waveform is generated due to blinking but is not generated due to eye nystagmus.

In general, the blinking frequency is defined as a value obtained by counting the number of peaks per unit time from the potential change waveform obtained by the above-mentioned method, or counting the number of peaks for a predetermined period of time and converting the count value into a value per unit time.

The eye movement data is easily influenced by a disturbance. For example, when a cord for the living body electrode swings due to a body movement, the base line fluctuation of the signal waveform occurs, and the eye movement waveform is disordered. When the electrode is adapted to a living body, the base line value tends to fluctuate.

Figure 38:
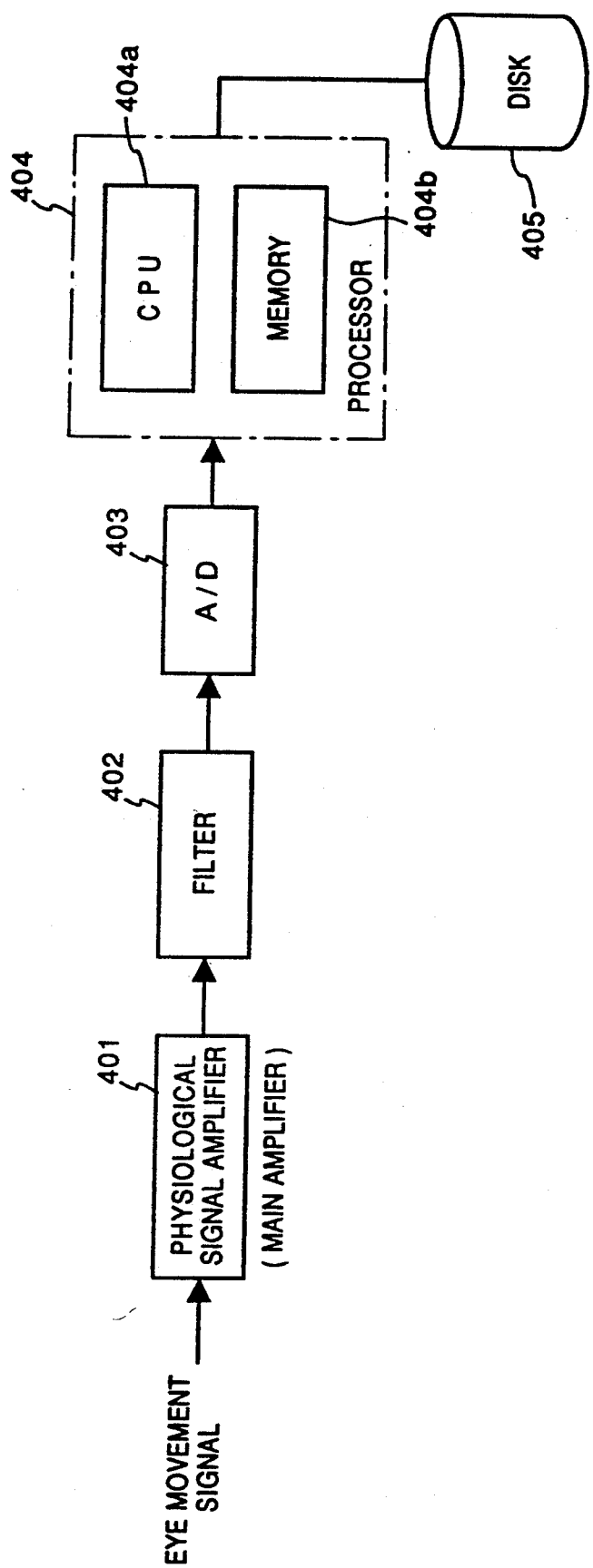

FIG. 38 is a block diagram showing an arrangement of a device for obtaining eye movement data. In FIG. 38, an eye movement signal from the living body electrode is input to a physiological signal amplifier 401, and the output from the amplifier 401 is filtered through a filter 402, e.g., an antialiasing filter. Thereafter, the output from the filter 402 is input to an A/D converter 403. A signal converted into a digital signal by the A/D converter 403 is stored in a memory 404b in a processor 404 as time-series data of the eye movement.

A CPU 404a constituting the processor 404 sets a statistically optimal trigger value on the basis of the processing flow (to be described later), and calculates the blinking frequency. The calculation result is stored in a disk 405 as a memory medium.

Figure 39:
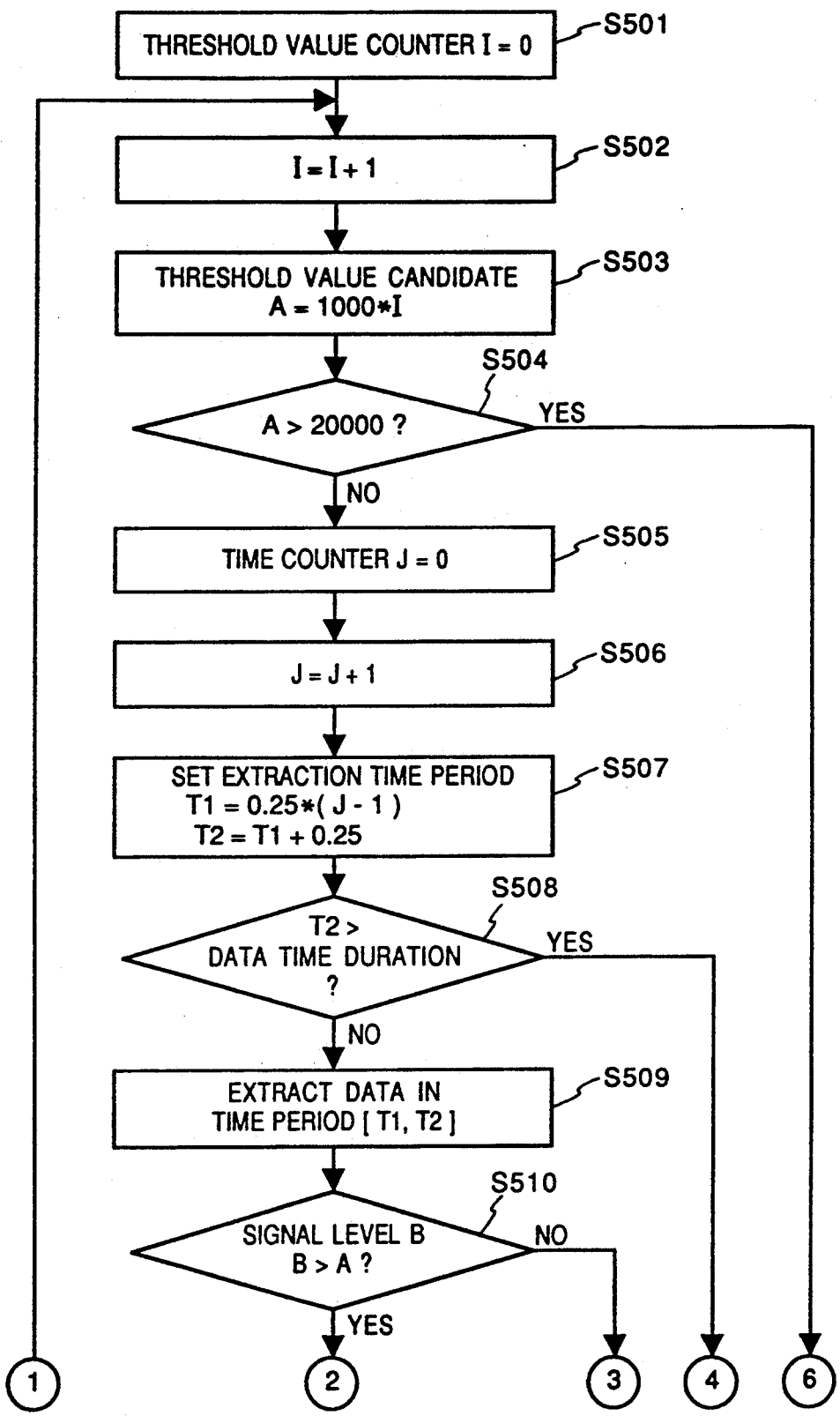
Figure 40:
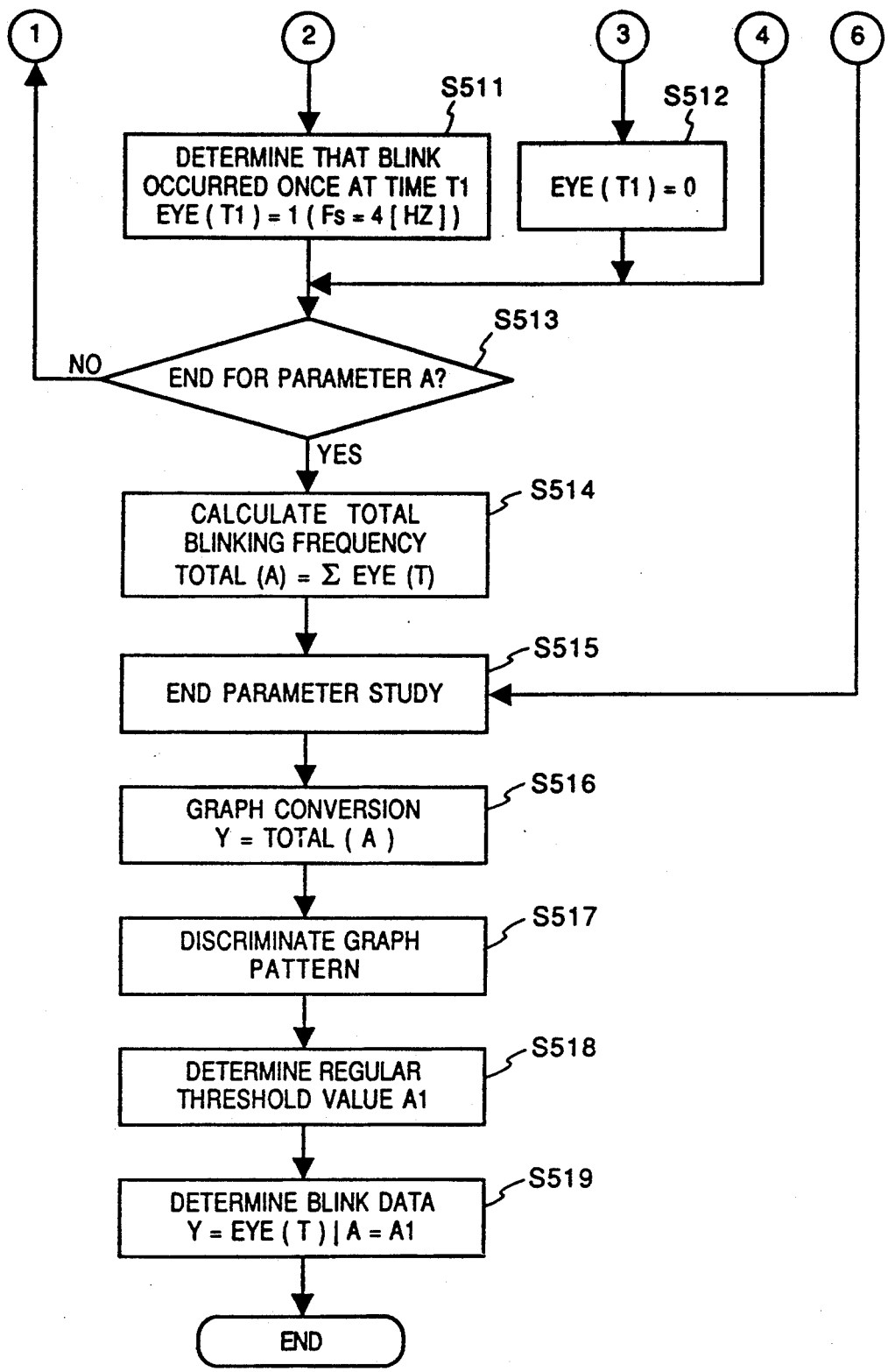

FIGS. 39 and 40 are flow charts showing a processing sequence for obtaining the blinking frequency. In FIG. 39, in step S501, a threshold value counter I is initialized, and in step S502, the counter I is incremented by 1 so as to select the next threshold value. In step S503, a threshold value candidate is determined, i.e., a temporary trigger value is changed from a considerably large upper-limit value of the eye movement data to 0. In this case, a value obtained by multiplying the counter value I with 1,000 is used as a candidate value A. In a method of changing the temporary trigger value, an interval for changing data is sufficiently finely divided, and the divided sub-intervals are used as units of the change in trigger value. The trigger value is changed by decreasing it from the upper-limit setting value to 0 in units of these sub-intervals.

In step S504, a value "20,000" is set with respect to the maximum value "32,768" corresponding to input 16-bit data, and it is checked if the candidate value A exceeds the value "20,000". In step S505, a time counter J is initialized, and in step S506, the counter J is incremented by 1.

In step S507, a waveform extraction time period [T1, T2] is set so as not to count a single blink a plurality of number of times. More specifically, a time duration in which blinks do not successively occur is set to be about 0.25 seconds, and data before and after this time are extracted. More specifically, a period [T1, T2] = [0.25·(J − 1), T1 + 0.25] is set. In step S508, it is checked if the above-mentioned T2 exceeds the time duration of data. If NO in step S508, data in the time period [T1, T2] is extracted.

In step S510, it is checked if a signal level B of the data extracted in step S509 is larger than the above-mentioned candidate value A. If YES in step S510, i.e., if the voltage level of the eye movement exceeds the temporary trigger value, the flow advances to step S511, and it is determined that a blink occurred once at a time T1. Then, 1 is set in a memory EYE(T1), thus storing an occurrence of a blink.

On the other hand, if it is determined in step S510 that the signal level B is smaller than the candidate value A, 0 is set in the memory EYE(T1) in step S512 to store that no blink occurs.

It is checked in step S513 if a blinking count for the candidate value A (parameter A) set in step S503 is completed. More specifically, the blinking count is performed for all the eye movement data on the basis of the temporary trigger value, and the total number of detected blinks is stored in the memory. If NO in step S513, the flow returns to step S502, and the same processing is performed by changing the temporary trigger value.

Figure 41:
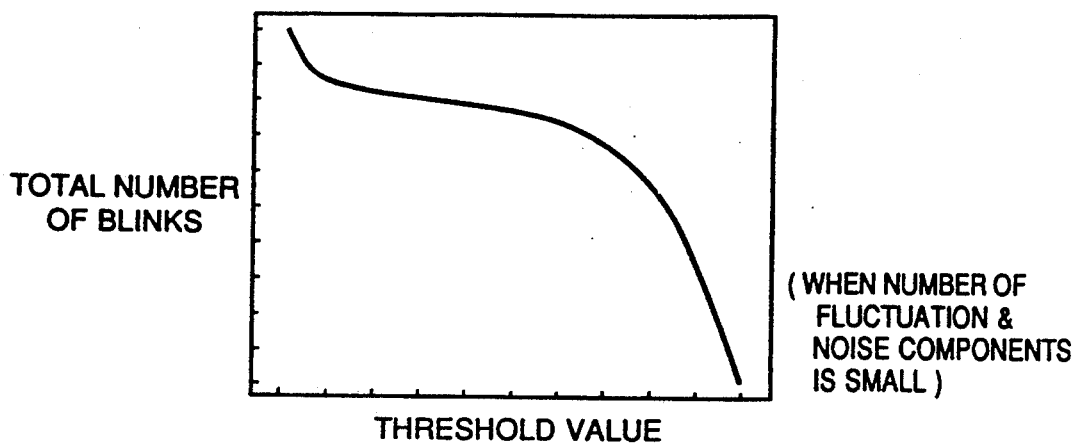
Figure 42:
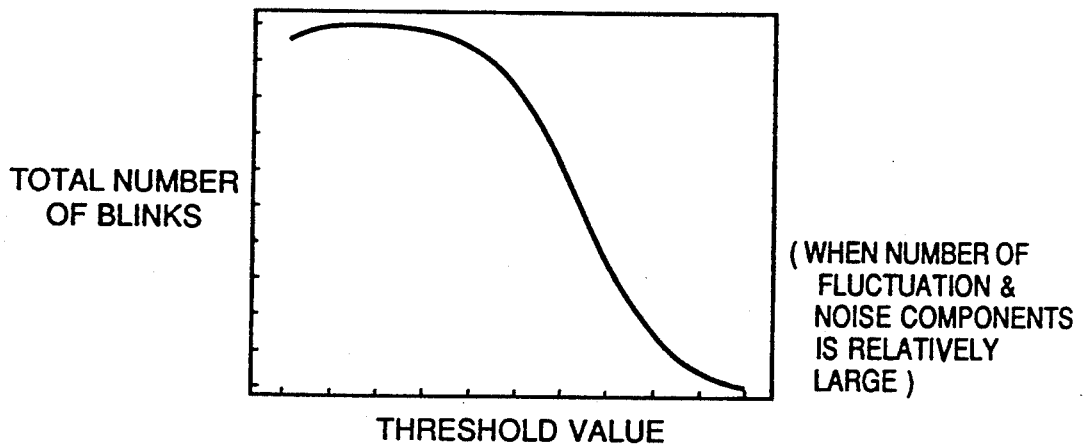
Figure 43:
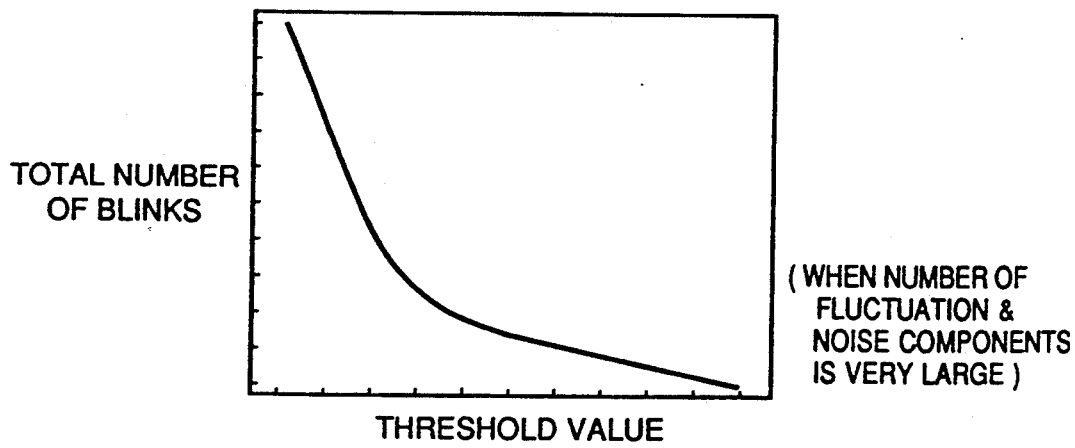

In step S514, the blinking frequency is calculated based on the total number of blinks obtained by the above-mentioned processing, and in step S515, processing for the parameter A is ended. In step S516, the relationship between the temporary trigger value and the total number of blinks is converted into a graph, as shown in FIGS. 41 to 43. In step S517, the graph pattern is discriminated, and in step S518, a regular threshold value is determined. Thereafter, blink data is determined in step S519.

Determination of the blink data will be described in detail below.

As described above, of the graphs of the obtained temporary trigger value and the total number of blinks, in the graph shown in FIG. 41, a portion where the gradient of the curve is small, i.e., a stable region, is present, and this portion can be considered as a statistically optimal trigger value. Under the optimal trigger value, the above-mentioned waveform extraction period is set. When the eye ball voltage level in this period exceeds the optimal trigger value, it is determined that a blink occurs, and the corresponding time is stored in the memory. Finally, the count value of the number of blinks per unit time is determined as the blinking frequency.

As shown in FIG. 42, when data includes the influence of a disturbance, since data obtained by measuring the eye movement is not suitable for evaluation, the gradient of the stable region becomes steep. Furthermore, when data is completely not suitable, no stable region is present, as shown in FIG. 43.

In this manner, whether or not the time-series data of all the eye movements, i.e., eye movement measurement data obtained by observing a change over time in eye movement for a long period of time is suitable for evaluation can be statistically determined, and stable blinking frequency data can be obtained with high precision.

<Increase/decrease in Stimulus in Low Waking Degree State>

In order to enhance the biological feedback effect, as a method of increasing/decreasing a stimulus amount according to a recovered amount of the waking degree (stimulus effect) with respect to the stimulus, an increase/decrease in stimulus amount in a low waking degree state will be explained below.

Figure 44:
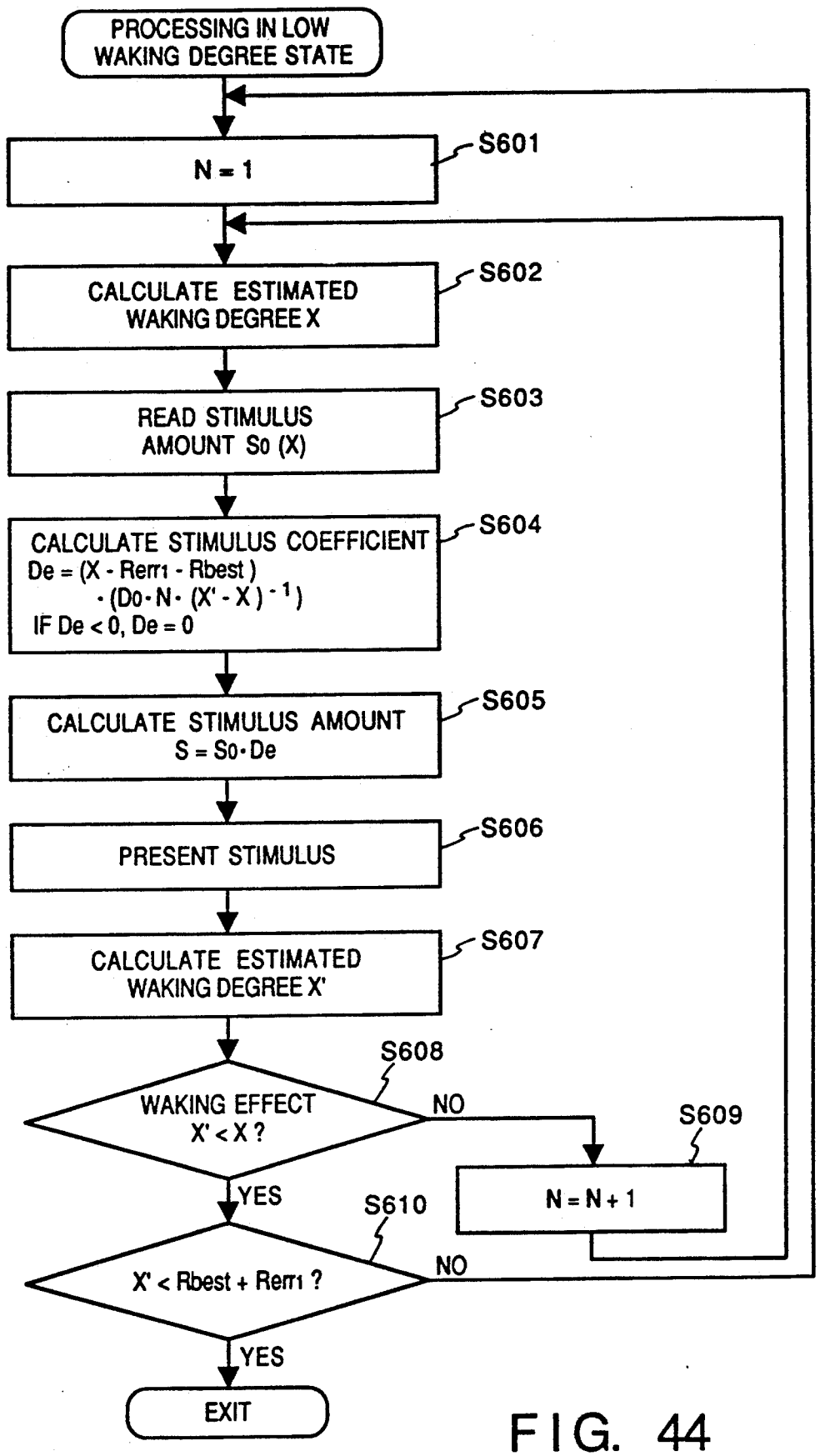
FIGS. 44 to 47 are views for explaining an increase/decrease in stimulus when the waking degree drops.
Figure 45:
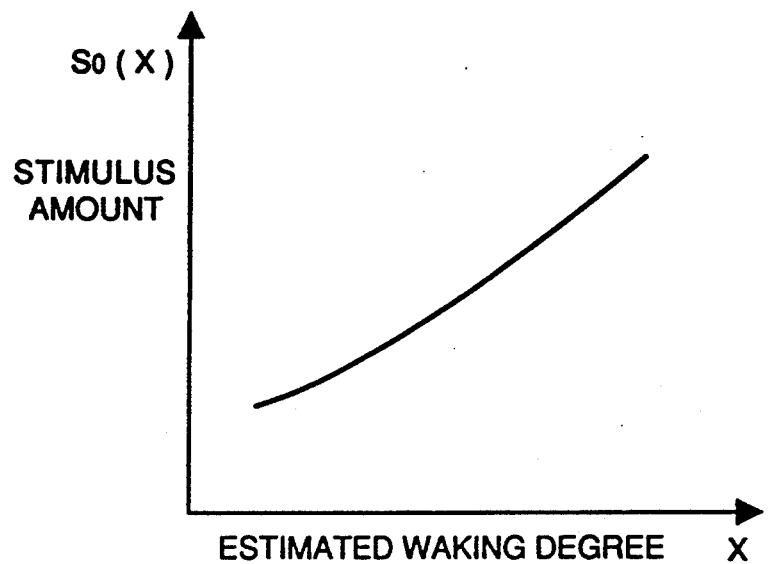

FIG. 44 is a flow chart showing stimulus increase/decrease processing in a low waking degree state. Prior to the processing shown in FIG. 44, a graph showing the relationship between the estimated waking degree and the corresponding stimulus amount, as shown in FIG. 45, or a formula representing the relationship therebetween is prepared.

In the flow chart shown in FIG. 44, in step S601, 1 is set in a time weighting counter N, and in step S602, the estimated waking degree X is calculated. In step S603, a stimulus amount SO(X) to be given to a driver is read from the graph shown in FIG. 45 according to the calculated estimated waking degree X.

In step S604, a stimulus coefficient De for adjusting the stimulus amount according to the recovered amount of the waking degree in response to the stimulus is calculated. The stimulus coefficient is a weighting coefficient for a stimulus to be generated, and is given by the following equation (11). In step S605, a stimulus amount is calculated using equation (12).

$$De = (X - Rerr1 - Rbest) \cdot (DO \cdot N \cdot (X' - X)^{-1}) \quad (11)$$

where $DO \cdot N \cdot (X' - X)^{-1}$ is the weighting coefficient ($W(t)$), and in general, it can be arbitrarily set as a function of $W(t, X' - X)$. Note that DO is a constant.

$$S = SO \cdot De \quad (12)$$

Figure 46:
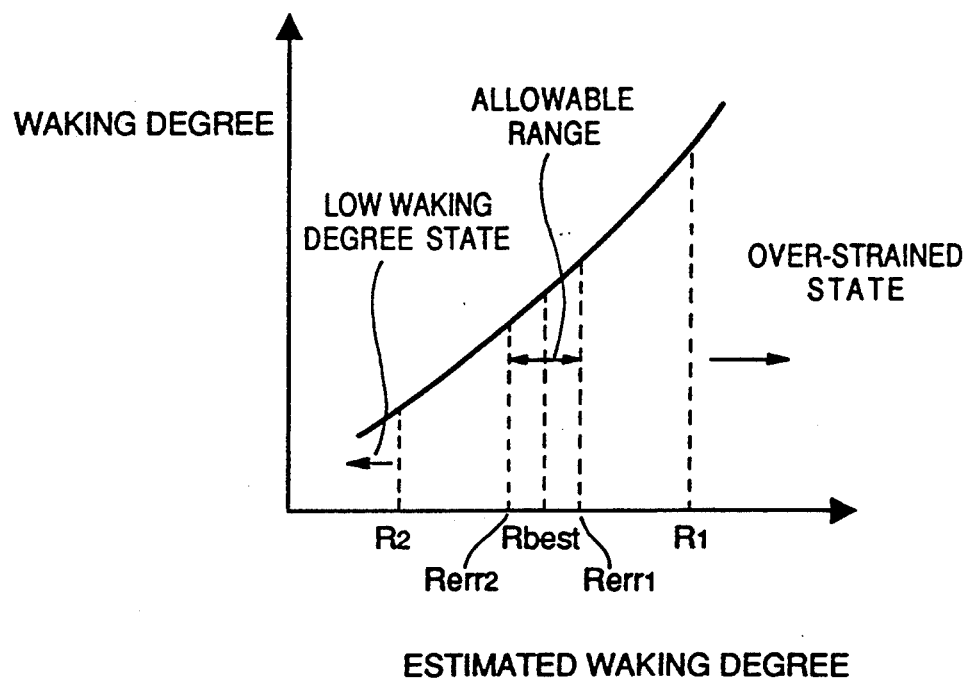

The feature of De is that it depends on N and $(X' - X)$. $X'$ is the estimated waking degree upon presentation of a stimulus after the processing in step S605, and $(X' - X)$ is an amount proportional to the change rate of the estimated waking degree. Furthermore, $(X - Rerr1 - Rbest)$ is a factor serving to adjust the stimulus amount according to the shift amount from a range in which an optimal waking state can be determined, as shown in the relationship between the waking degree and the estimated waking degree in FIG. 46.

In the stimulus coefficient, to multiply the factor $(X' - X)^{-1}$ implies that a larger amount of stimulus is presented as the change in waking degree by the stimulus effect is smaller.

In step S606, the stimulus amount calculated in step S605 is presented, and in step S607, the estimated waking degree $X'$ after presentation of the stimulus is calculated. In step S608, it is checked if the stimulus presented in step S606 is effective. That is, if $X' < X$, it is determined that the stimulus is effective. Contrary to this, if $X' \geq X$, it is determined that the stimulus is not effective, and the flow advances to step S609 to increment the value N by 1. Thereafter, the flow returns to step S602. The counter N is a loop counter, and as the loop of this processing system is executed a larger number of times, the content of the counter N is increased to increase the stimulus coefficient. N is an amount proportional to the time, and this means to increase the stimulus amount when the stimulus effect cannot be obtained after an elapse of time.

When the stimulus effect can be confirmed, it is checked in step S610 if the optimal waking state is recovered by the stimulus effect. In this case, X' and (Rerr1 + Rbest) are compared with each other. If X' < (Rerr1 + Rbest) is satisfied, it is determined that the waking effect is obtained, and the control escapes from this processing system. However, if it is determined that no waking effect is obtained, the flow returns to step S601.

<Increase/decrease in Stimulus in Strained State>

As for an increase/decrease in stimulus amount in a strained state, the processing method is basically the same as that in the low waking degree state.

Figure 47:
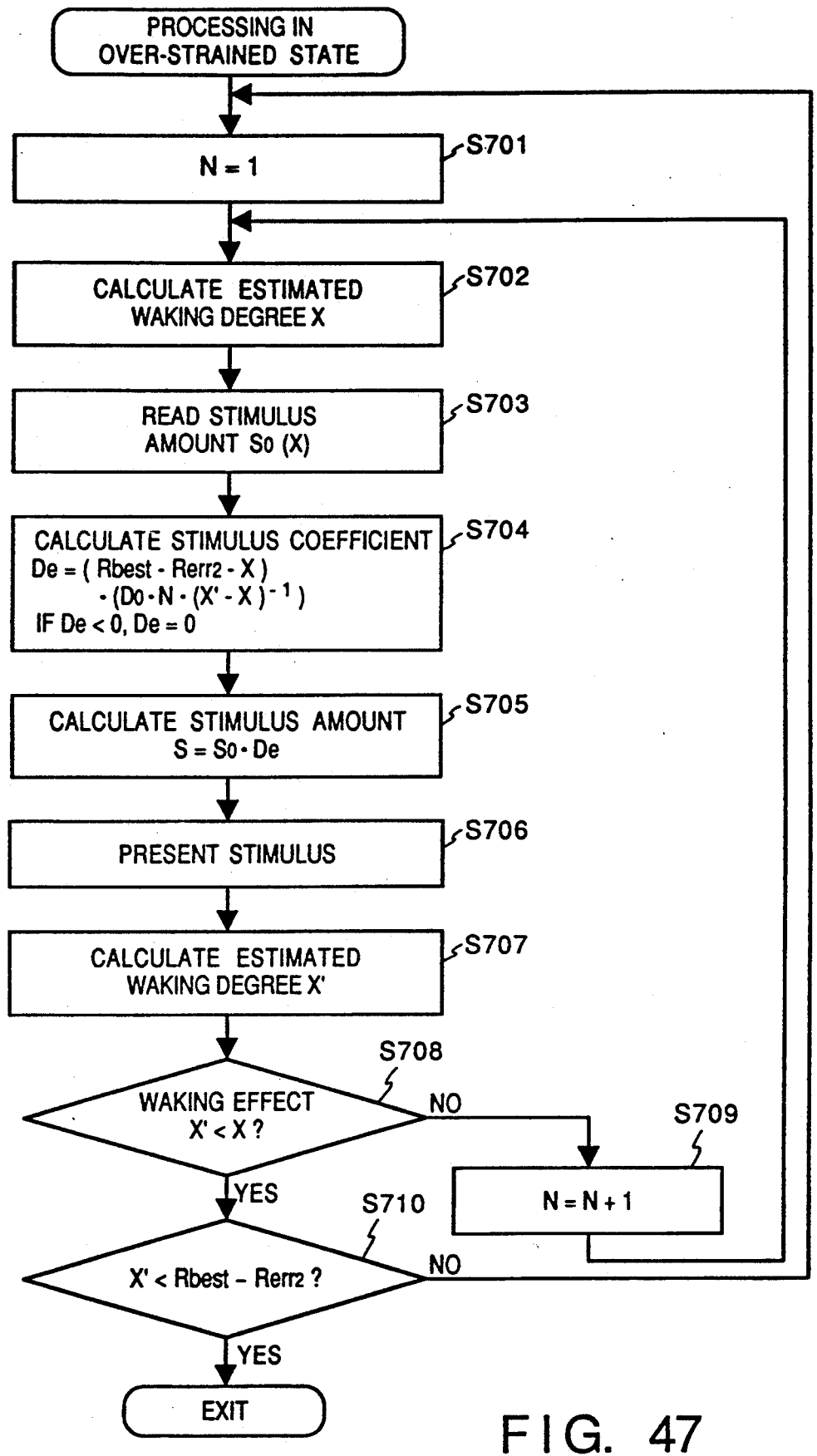

More specifically, in this case, prior to the processing in a strained state shown in FIG. 47, the graph showing the relationship between the estimated waking degree and the corresponding stimulus amount, as shown in FIG. 45, or a formula representing the relationship therebetween is prepared.

In the flow chart shown in FIG. 47, in the same manner as in the processing in the low waking degree state, in step S701, 1 is set in the time weighting counter N, and in step S702, the estimated waking degree X is calculated. In step S703, a stimulus amount SO(X) to be given to a driver is read from the graph shown in FIG. 45 according to the calculated estimated waking degree X.

In step S704, a stimulus coefficient De for adjusting the stimulus amount according to the recovered amount of the waking degree in response to the stimulus is calculated. The stimulus coefficient is a weighting coefficient for a stimulus to be generated, and is given by the following equation (13). In step S705, a stimulus amount is calculated using equation (12).

$$De = (Rbest - Rerr2 - X) \cdot (DO \cdot N \cdot (X' - X)^{-1}) \quad (13)$$

where $DO \cdot N \cdot (X' - X)^{-1}$ is the weighting coefficient (W(t)), and in general, it can be arbitrarily set as a function of W(t, X' - X). Note that DO is a constant.

In this case, De also depends on N and (X' - X). X' is the estimated waking degree upon presentation of a stimulus after the processing in step S705, and (X' - X) is an amount proportional to the change rate of the estimated waking degree. Furthermore, (X - Rerr1 - Rbest) is a factor serving to adjust the stimulus amount according to the shift amount from a range in which an optimal waking state can be determined, as shown in the relationship between the waking degree and the estimated waking degree in FIG. 46.

In the stimulus coefficient, to multiply the factor $(X' - X)^{-1}$ implies that a larger amount of stimulus is presented as the change in waking degree by the stimulus effect is smaller.

In step S706, the stimulus amount calculated in step S705 is presented, and in step S707, the estimated waking degree X' after presentation of the stimulus is calculated. In step S708, it is checked if the stimulus presented in step S706 is effective. That is, if X' < X, it is determined that the stimulus is effective. Contrary to this, if X' ≧ X, it is determined that the stimulus is not effective, and the flow advances to step S709 to increment the value N by 1. Thereafter, the flow returns to step S702. The counter N is a loop counter, and as the loop of this processing system is executed a larger number of times, the content of the counter N is increased to increase the stimulus coefficient. N is an amount proportional to the time, and this means to increase the stimulus amount when the stimulus effect cannot be obtained after an elapse of time.

When the stimulus effect can be confirmed, it is checked in step S710 if the optimal waking state is recovered by the stimulus effect. In this case, X' and (Rbest − Rerr2) are compared with each other. If X' < (Rbest − Rerr2) is satisfied, it is determined that the waking effect is obtained, and the control escapes from this processing system. However, if it is determined that no waking effect is obtained, the flow returns to step S701.

As described above, the apparatus of this embodiment can quantitatively obtain an estimated waking degree with high precision on the basis of the correlation between the brain waves and the reaction time or between the blinking frequency and the reaction time. When a stimulus is presented according to the obtained waking degree, a drop in waking degree of a person can be prevented, and the person can be maintained in an optimal waking state.

Not only in a low waking degree state, but also in an over-strained state, the waking degree of a person can be recovered to a normal state.

In the above embodiment, the estimated waking degree is calculated based on the brain waves or the blinking frequency. However, the present invention is not limited to this. For example, the waking degree may be estimated based on the heart rate.

As many apparently widely different embodiments of the present invention can be made without departing from the spirit and scope thereof, it is to be understood that the invention is not limited to the specific embodiments thereof except as defined in the appended claims.

What is claimed is:

1. A waking degree maintaining apparatus comprising:
   stimulus means for presenting a predetermined stimulus to a person in order to maintain the person in a waking state;
   first detection means for detecting a reaction time to the predetermined stimulus;
   second detection means for detecting a quantity which represents a physiological condition correlating to a waking degree of the person;
   first generation means for generating an estimated waking degree of the person, based upon the reaction time and the quantity;
   second generation means for generating an average value and a standard deviation of a distribution of a plurality of said estimated waking degrees; and
   determination means for determining a drop in waking degree in conformity with the average value and the standard deviation, and for causing said stimulus means to present a predetermined stimulus to the person, when the drop in waking degree is determined, so as to maintain the person in a waking state.

2. The apparatus according to claim 1, wherein said second detection means further comprises means for detecting brain waves as the quantity representing the physiological condition of the person, and said first generation means generates the estimated waking degree based upon the brain waves and the reaction time.

3. The apparatus according to claim 1, wherein said second detection means further comprises means for detecting a blinking frequency as the quantity representing the physiological condition of the person, and said first generation means generates the estimated waking degree based upon the blinking frequency and the reaction time.

4. The apparatus according to claim 3, wherein the means for detecting the blinking frequency sets a blink discrimination threshold value from a stable region of a statistical distribution of blink potential peaks, and the blinking frequency is detected by comparing eye movements to the threshold value.

5. The apparatus according to claim 1, wherein said second detection means further comprises means for detecting a heart rate as the quantity representing the physiological condition of the person, and said first generation means generates the estimated waking degree based upon the heart rate and the reaction time.

6. A waking degree maintaining apparatus comprising:
   stimulus means for presenting a predetermined stimulus to a person;
   first detection means for detecting a reaction time to the predetermined stimulus;
   second detection means for detecting a quantity which represents a physiological condition correlating to a waking degree of the person;
   first generation means for generating an estimated waking degree of the person, based upon the reaction time and the quantity;
   second generation means for generating a period of a waking degree rhythm and a standard deviation of a distribution of a plurality of said estimated waking degrees; and
   determination means for determining a drop in waking degree in conformity with the period and the standard deviation, and for causing said stimulus means to present a predetermined stimulus to the person, when the drop in waking degree is determined, so as to maintain the person in a waking state.

7. The apparatus according to claim 6, wherein said second detection means further comprises means for detecting brain waves as the quantity representing the physiological condition of the person, and said first generation means generates the estimated waking degree based upon the brain waves and the reaction time.

8. The apparatus according to claim 6, wherein said second detection means further comprises means for detecting a blinking frequency as the quantity representing the physiological condition of the person, and said first generation means generates the estimated waking degree based upon the blinking frequency and the reaction time.

9. The apparatus according to claim 8, wherein the means for detecting the blinking frequency sets a blink discrimination threshold value from a stable region of a statistical distribution of blink potential peaks, and the blinking frequency is detected by comparing eye movements to the threshold value.

10. The apparatus according to claim 6, wherein said second detection means further comprises means for detecting a heart rate as the quantity representing the physiological condition of the person, and said first generation means generates the estimated waking degree based upon the heart rate and the reaction time.

11. The apparatus according to claim 6, wherein the period of the waking degree rhythm is measured with reference to an amplitude base value obtained from upper-limit average peak values and lower-limit average peak values of amplitudes of the waking degree, which are for determining the beginning of the drop in the waking degree.

12. A waking degree maintaining apparatus comprising:
   first detection means for detecting a reaction time to a stimulus presented to a person;
   second detection means for detecting a quantity which represents a physiological condition correlating to a waking degree of the person;
   generation means for generating an estimated waking degree of the person, based upon the reaction time and the quantity;
   means for setting a stimulus amount according to the estimated waking degree; and
   means for presenting a stimulus corresponding to the set stimulus amount.

13. The apparatus according to claim 12, further comprising correction means for correcting the stimulus amount according to a change in the estimated waking degree upon previous presentation of the stimulus.

14. The apparatus according to claim 13, wherein said correction means generates a correction coefficient for adjusting a stimulus in a low waking degree state according to a recovered amount of the waking degree caused by the stimulus.

15. The apparatus according to claim 13, wherein said correction means generates a correction coefficient for adjusting a stimulus in a strained state according to a recovered amount of the waking degree by the stimulus.

* * * * *

UNITED STATES PATENT AND TRADEMARK OFFICE
CERTIFICATE OF CORRECTION

PATENT NO. : 5,311,877
DATED : MAY 17, 1994
INVENTOR(S) : Atsuhide KISHI

It is certified that error appears in the above-indentified patent and that said Letters Patent is hereby corrected as shown below:

Col. 11, line 5, "B $\lambda_o$" should be --B$\ell_o$--;
line 60, "B$\lambda_o$" should be --B$\ell_o$--;
line 64, "B$\lambda_1$" should be --B$\ell_1$--;
line 66, "B$\lambda_1$" should be --B$\ell_1$--.

Col. 12, line 1, "B$\lambda_o$ and B$\lambda_1$" should be --B$\ell_o$ and B$\ell_1$--;
line 9, "B$\lambda_1$" should be --B$\ell_1$--;
line 14, "B$\lambda_1$ and B$\lambda_2$" should be --B$\ell_1$ and B$\ell_2$--;
line 18, "B$\lambda_1$ and B$\lambda_2$" should be --B$\ell_1$ and B$\ell_2$--;
line 23, "B$\lambda_2$" should be --B$\ell_2$--;
line 27, "B$\lambda_o$ and B$\lambda_1$" should be --B$\ell_o$ and B$\ell_1$--;
line 47, "B$\lambda_o$" (both occurrences) should be --B$\ell_o$--.

Col. 13, line 7, "B$\lambda_1$" (both occurrences) should be --B$\ell_1$--;
line 12, "B$\lambda_2$." should be --B$\ell_2$.--;
line 15, "B$\lambda_2$" should be --B$\ell_2$--.

UNITED STATES PATENT AND TRADEMARK OFFICE
CERTIFICATE OF CORRECTION

PATENT NO. : 5,311,877
DATED : MAY 17, 1994
INVENTOR(S) : Atsuhide KISHI

It is certified that error appears in the above-indentified patent and that said Letters Patent is hereby corrected as shown below:

Col. 15,     line 18, (Equation (4)), "A$\lambda$" should be --A$\ell$--;
               line 21, "A$\lambda$" should be --A$\ell$--;
               line 28, "A$\lambda$" should be --A$\ell$--;
               line 43, "A$\lambda$" should be --A$\ell$--;
               line 44, "A$\lambda$" should be --A$\ell$--.

Col. 17,     line 22, (Equation 10), "T$\lambda$" should be --T$\ell$--;
               line 24, "T$\lambda$" should be --T$\ell$--;
               line 32, "T$\lambda$" should be --T$\ell$--.

Signed and Sealed this

Twenty-fifth Day of July, 1995

Attest:

BRUCE LEHMAN

*Attesting Officer*      *Commissioner of Patents and Trademarks*